United States Patent
Zia et al.

(10) Patent No.: US 12,234,242 B2
(45) Date of Patent: *Feb. 25, 2025

(54) RADIOPHARMACEUTICALS, RADIOIMAGING AGENTS, AND USES THEREOF

(71) Applicant: Clarity Pharmaceuticals Ltd, Eveleigh (AU)

(72) Inventors: Nicholas Alan Zia, Melbourne (AU); Paul Stephen Donnelly, Melbourne (AU)

(73) Assignee: Clarity Pharmaceuticals Ltd, Eveleigh (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/233,135

(22) Filed: Aug. 11, 2023

(65) Prior Publication Data

US 2023/0382918 A1 Nov. 30, 2023

Related U.S. Application Data

(63) Continuation of application No. 17/834,773, filed on Jun. 7, 2022, now Pat. No. 11,970,503, which is a continuation of application No. 17/198,131, filed on Mar. 10, 2021, now Pat. No. 11,384,088, which is a continuation of application No. 16/619,073, filed as application No. PCT/AU2018/050555 on Jun. 5, 2018, now Pat. No. 10,975,089.

(30) Foreign Application Priority Data

Jun. 6, 2017 (AU) ................................ 2017902151

(51) Int. Cl.
| | |
|---|---|
| C07D 487/08 | (2006.01) |
| A61K 9/00 | (2006.01) |
| A61K 33/34 | (2006.01) |
| A61K 51/04 | (2006.01) |
| A61K 51/06 | (2006.01) |
| C07F 1/08 | (2006.01) |
| C07F 1/00 | (2006.01) |

(52) U.S. Cl.
CPC .......... *C07D 487/08* (2013.01); *A61K 9/0019* (2013.01); *A61K 33/34* (2013.01); *A61K 51/0497* (2013.01); *A61K 51/06* (2013.01); *C07F 1/08* (2013.01); *C07F 1/00* (2013.01)

(58) Field of Classification Search
CPC ...... A61K 51/0497; C07F 1/10; C07D 487/08
See application file for complete search history.

(56) References Cited

U.S. PATENT DOCUMENTS

2011/0293517 A1 12/2011 Donnelly

FOREIGN PATENT DOCUMENTS

WO WO-2013/082656 6/2013

OTHER PUBLICATIONS

Gourni et al, "Copper-64 Labeled Macrobicyclic Sarcophagine Coupled to a GRP Receptor Antagonist Shows Great Promise for PET Imaging of Prostate Cancer", Mol. Pharmaceuticals (2015) 12, 2781-2790.
Guidelines for conducting preclinical drug trials, edited by Mironov A.N., Part One, M .: Grif and K, 2012, 944 pp., in particular, chapter 39.
Huang et al, "Design, synthesis and validation of integrin a2B1-targeted probe for microPET imaging of prostate cancer" Eur J Nucl Med Mol Imaging (2011) 38:1313-1322.
Kharkevich D.A., Pharmacology, 10th ed. M: GEOTAR-Media, 2010, pp. 73-74.
Korolyuk I.P. et al., Radiation diagnostics, Textbook, 3rd ed., Revised and supplemented, M .: BINOM publishing house , 2015, 496 pp., see pp. 103-104.
Liu et al, "Development of Multi-Functional Chelators Based on Sarcophagine Cages", Molecules (2014) 19, 4246-4255.
Paterson et al, "PET imaging of tumours with a 64Cu labeled macrobicyclic cage amine ligand tethered to Tyr3-octreotate", Dalton Trans (2014) 43, 1386-1396.
V.N. Zhulenko, G.I. Gorshkov, Pharmakologia [Pharmacology]. M.: KolosS, 2008, pp. 34-35.

*Primary Examiner* — James W Rogers
(74) *Attorney, Agent, or Firm* — Morrison & Foerster LLP

(57) ABSTRACT

The present invention relates to compounds that are useful as radiopharmaceuticals and radioimaging agents which bear a radionuclide-chelating agent. These coordinated compounds are useful in radiotherapy and diagnostic imaging. The invention also relates to methods of diagnosis, prognosis and therapy utilising the non-coordinated and radiolabelled compounds of the invention.

20 Claims, 8 Drawing Sheets

| | Mouse 1 | Mouse 2 | Mouse 3 | Mouse 4 |
|---|---|---|---|---|
| 30 min |  SUVmax 0.84 |  SUVmax 0.66 |  SUVmax 1.02 |  SUVmax 1.31 |
| 2 hr |  SUVmax 1.12 |  SUVmax 0.55 |  SUVmax 0.92 |  SUVmax 0.97 |
| 22 hr |  SUVmax 0.30 |  SUVmax 0.21 |  SUVmax 0.21 |  SUVmax 0.27 |

PSMA-617

PSMA-11

PSMA I&T

RADIOPHARMACEUTICALS, RADIOIMAGING AGENTS, AND USES THEREOF

CROSS REFERENCE TO RELATED APPLICATIONS

This application is a continuation of U.S. patent application Ser. No. 17/834,773, filed Jun. 7, 2022, now allowed, which is a continuation of U.S. patent application Ser. No. 17/198,131, filed Mar. 10, 2021, now issued as U.S. Pat. No. 11,384,088, issued Jul. 12, 2022, which is a continuation of U.S. patent application Ser. No. 16/619,073, filed Dec. 3, 2019, now issued as U.S. Pat. No. 10,975,089, issued Apr. 13, 2021, which is a national stage application under 35 U.S.C. § 371 of International Application No. PCT/AU2018/050555, filed internationally on 5 Jun. 2018 which claims Benefit of Australian Application No. 2017902151, filed on 6 Jun. 2017, the contents of which are incorporated herein by reference in their entirety.

FIELD

The present invention relates to compounds that are useful as radiopharmaceuticals and radioimaging agents which bear a radionuclide-chelating agent. These coordinated compounds are useful in radiotherapy and diagnostic imaging. The invention also relates to methods of diagnosis, prognosis and therapy utilising the non-coordinated and radiolabelled compounds of the invention.

BACKGROUND

Prostate cancer is a leading cause of cancer-related deaths in men, with the mortality rate often attributed to difficulties in the detection and subsequent treatment of the disease. Prostate-related tumours often show increased expression of prostate-specific membrane antigen (PSMA), which is an enzyme typically expressed in prostate tissue but is often upregulated in some prostate cancers. This means that PSMA is a good biomarker or target for imaging, diagnostic, prognostic purposes. However since PSMA is also expressed in other tissues, both normal and malignant, difficulties exist in successfully imaging prostate cancer.

Radiolabelled compounds may be used as a radiopharmaceutical or radioimaging agent, if the compound can bind sufficiently to the desired site and also deliver a radionuclide to the same site for the purposes of imaging or therapy.

Compounds or ligands containing a urea-based motif, such as the glutamate-substituted urea below are known to bind to the catalytic site of PSMA with good affinity.

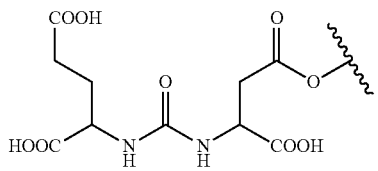 [SMILES: *OC(=O)CC(NC(=O)NC(CCC(=O)O)C(=O)O)C(=O)O]

While compounds bearing this or similar motifs have been synthesised, problems relating to their stability or binding behaviour in vivo have been observed. For a compound to be useful in radioimaging or radiotherapy, the compound and the resultant complex comprising a radionuclide needs to be stable in vivo. One of the known problems associated with radiolabelled compounds is that the complex formed with the radionuclide is not sufficiently strong and the radionuclide "leaks" out of the complex and is not delivered to the intended site. Further problems that result from leakage of the radionuclides include the diffusion of the radionuclide to unwanted sites. This may lead to healthy tissue being damaged as a result of the activity of the radionuclide. Furthermore, the diffusion of the radionuclide leads to images of poorer quality, as the contrast between true binding sites (indicating the location of tumours) and sites with unwanted radionuclide is reduced.

Other problems associated with radiolabelled compounds include the possibility of radiolysis, where the radioisotope itself leads to the destruction of the compound and subsequent diffusion of the radionuclide. Radiolysis occurs as a result of the spontaneous decay of radionuclide, with the energy released leading to the cleavage of bonds in the ligand and destruction of the complex. Radiolysis also leads to the diffusion of the radionuclide to unwanted sites, which further contributes to the problems described above.

As the compound is to be administered to those in need, the compounds must also be inherently non-toxic to the subject. Another problem associated with the use of radiolabelled compounds for diagnosis, imaging and therapy is the issue of binding affinity. Where the binding affinity for the target, i.e. PSMA in this instance, is low, the complex may not achieve binding and be excreted, or may only show limited binding. Where the complex is immediately excreted, this leads to a reduction in overall efficacy. However where the compound shows limited excretion and limited binding, the complex may diffuse throughout the subject and lead to the unwanted effects described above.

Furthermore, limited binding of the complex will likely reduce the time available for acceptable imaging or treatment of the tumour.

There exists a need for compounds that can provide the desired binding affinity to prostate cancer-related tumours and also have the ability to provide the requisite imaging properties. There is also a requirement that the compounds are sufficiently stable and do not undergo decomposition during use.

SUMMARY OF THE INVENTION

The present invention relates to novel compounds that show improved binding affinity to PSMA. The present inventors have found that the use of an amino acid-substituted urea bound to a macrocyclic sarcophagine via specific linkers provides compounds that bind to PSMA and when complexed with a radionuclide, provide good/improved imaging properties.

In one aspect, the present invention provides a compound of Formula (I), or a salt, complex, isomer, solvate or prodrug thereof:

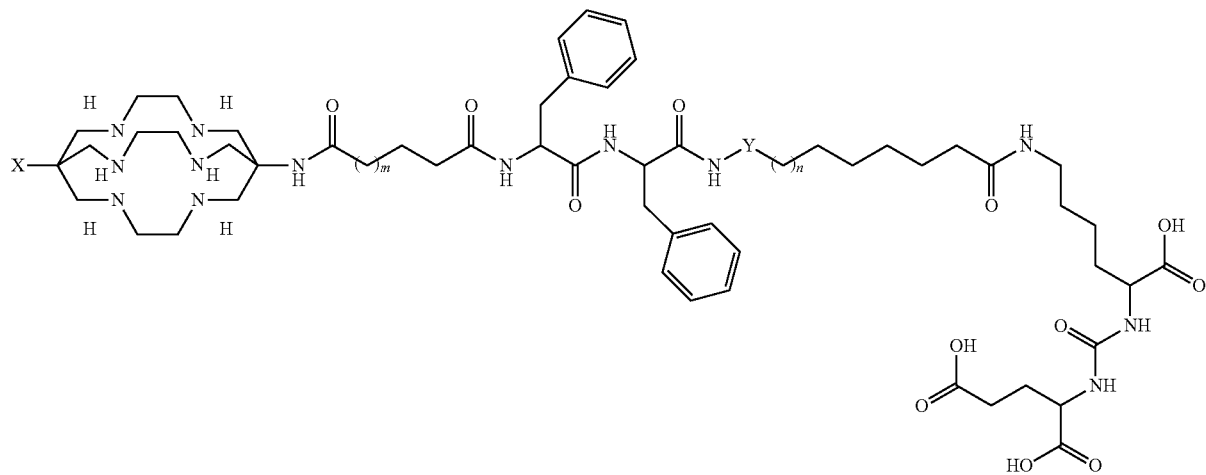

wherein:
X is a group selected from H, OH, halogen, cyano, NO$_2$, NH$_2$, optionally substituted C$_1$-C$_{12}$ alkyl, optionally substituted amino, optionally substituted amide and optionally substituted aryl;
Y is an optionally substituted C$_1$-C$_{12}$ alkylene group, wherein one or more of the methylene groups in the alkylene group may be further optionally substituted for a group selected from amido, carbonyl, urea and thiourea;
m is 0, 1, or 2; and
n is 0, 1, or 2.

In an embodiment, the compound, or a salt, complex, isomer, solvate or prodrug thereof, has the formula:

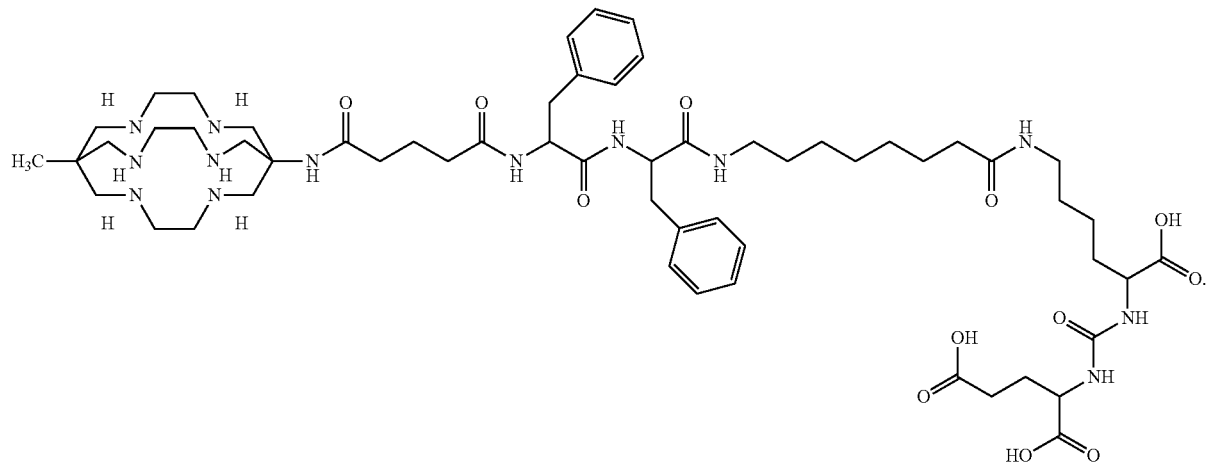

In another embodiment, the compound, or a salt, complex, isomer, solvate or prodrug thereof, has the formula:

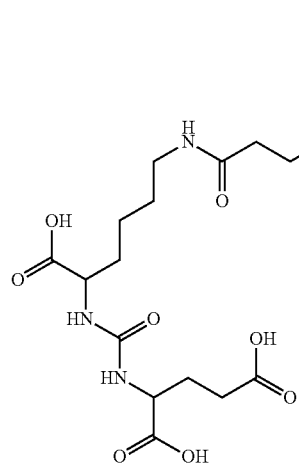
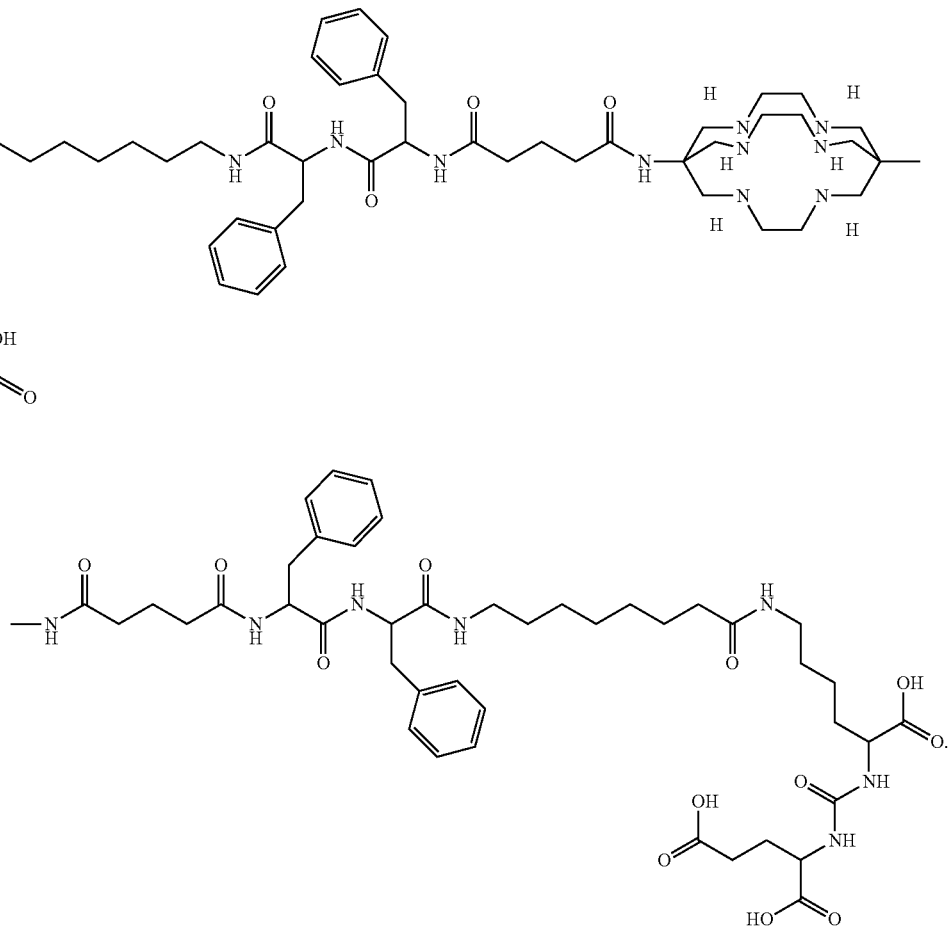

In another embodiment, the compound, or a salt, complex, isomer, solvate or prodrug thereof, has the formula:

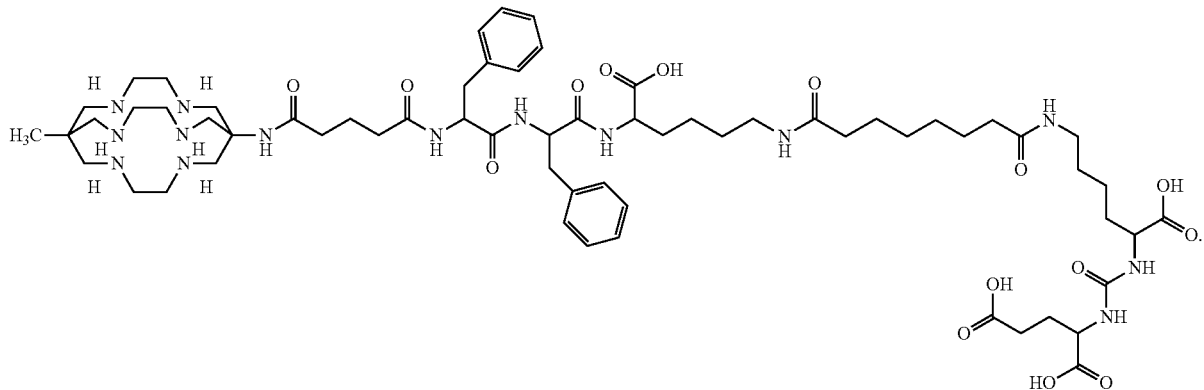

In another aspect, the present invention provides a composition comprising a compound according to an aforementioned aspect, and a pharmaceutically acceptable excipient.

In another aspect, the present invention provides an aqueous composition for parenteral administration comprising a compound of an aforementioned aspect; and wherein the composition further comprising ethanol, gentisic acid or a salt thereof, and sodium chloride.

In another aspect, the present invention provides a method for the treatment or prevention of a condition in a subject in need thereof, the method comprising administering a therapeutically effective amount of a compound according to an aforementioned aspect or a composition according to an aforementioned aspect.

DETAILED DESCRIPTION

Figure 1:
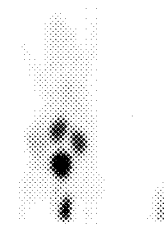
FIG. 1: PET imaging of LNCaPs bearing NSG mice treated with $^{64}$Cu-Sar-PSMA at 30 minutes, 2 hours and 22 hours.
Figure 1:
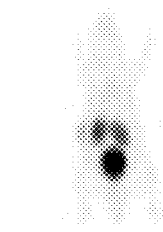
Figure 1:
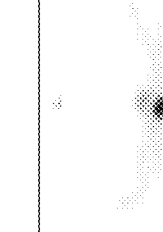
Figure 1:
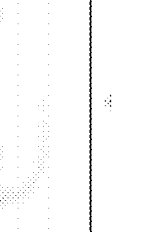
Figure 1:
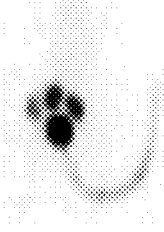
Figure 1:
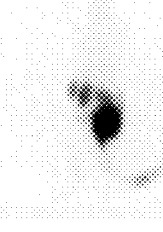
Figure 1:
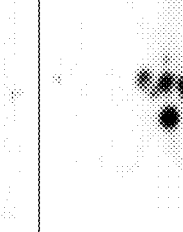
Figure 1:
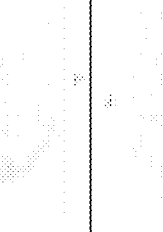
Figure 1:
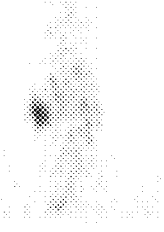
Figure 1:
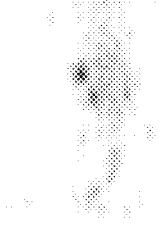
Figure 1:
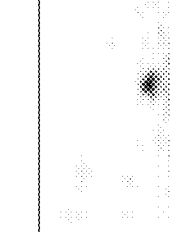
Figure 1:
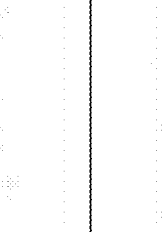

As described and shown herein, the present inventors have found that a compound comprising an amino acid substituted-urea joined to a sarcophagine cage via a linker group can bind to PSMA. Without wishing to be bound by theory, it is thought that the combination of the amino acid-urea fragment, the linker and the sarcophagine cage provides the advantages observed and discussed below.

The complexes as described herein are radiolabelled with a radionuclide or radioisotope that undergoes spontaneous decay, where these byproducts of decay are detected by various means, such as positron emission tomography (PET) or single-photon emission computed tomography (SPECT). The quality of the images obtained, and subsequently the confidence in any diagnosis based on these images, depend on the ability of the radiolabelled complex to specifically bind to the prostate cancer site.

As used herein, the term "sarcophagine" refers to the nitrogen-containing macrocyclic ligand with the formula 3,6,10,13,16,19-hexaazabicyclo[6.6.0]icosane.

The term "optionally substituted" as used throughout the specification denotes that the group may or may not be further substituted or fused (so as to form a condensed polycyclic system), with one or more non-hydrogen substituent groups. In certain embodiments the substituent groups are one or more groups independently selected from the group consisting of halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —C(=O)OH, —C(=O)R$^a$, —C(=O)OR$^a$, C(=O)NR$^a$R$^b$, C(=NOH)R$^a$, C(=NR$^a$)NR$^b$R$^c$, NR$^a$R$^b$, NR$^a$C(=O)R$^b$, NR$^a$C(=O)OR$^b$, NR$^a$C(=O)NR$^b$R$^c$, NR$^a$C(=NR$^b$)NR$^c$R$^d$, NR$^a$SO$_2$R$^b$, —SR$^a$, SO$_2$NR$^a$R$^b$, —OR$^a$, OC(=O)NR$^a$R$^b$, OC(=O)R$^a$ and acyl, wherein R$^a$, R$^b$, R$^c$ and R$^d$ are each independently selected from the group consisting of H, C$_1$-C$_{12}$alkyl, C$_1$-C$_{12}$haloalkyl, C$_2$-C$_{12}$alkenyl, C$_2$-C$_{12}$alkynyl, C$_2$-C$_{10}$ heteroalkyl, C$_3$-C$_{12}$cycloalkyl, C$_3$-C$_{12}$cycloalkenyl, C$_2$-C$_{12}$heterocycloalkyl, C$_2$-C$_{12}$ heterocycloalkenyl, C$_6$-C$_{18}$aryl, C$_1$-C$_{18}$heteroaryl, and acyl, or any two or more of R$^a$, R$^b$, R$^c$ and R$^d$, when taken together with the atoms to which they are attached form a heterocyclic ring system with 3 to 12 ring atoms.

In some embodiments, each optional substituent is independently selected from the group consisting of: halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkyloxy, alkyloxyalkyl, alkyloxyaryl, alkyloxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, —COOH, —SH, and acyl.

Examples of particularly suitable optional substituents include F, Cl, Br, I, CH$_3$, CH$_2$CH$_3$, OH, OCH$_3$, CF$_3$, OCF$_3$, —NO$_2$, NH$_2$, COOH, COOCH$_3$ and CN.

"Alkenyl" as a group or part of a group denotes an aliphatic hydrocarbon group containing at least one carbon-carbon double bond and which may be straight or branched preferably having 2-12 carbon atoms, more preferably 2-10 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl.

"Alkyl" as a group or part of a group refers to a straight or branched aliphatic hydrocarbon group, preferably a C$_1$-C$_{12}$ alkyl, more preferably a C$_1$-C$_{10}$ alkyl, most preferably C$_1$-C$_6$ unless otherwise noted. Examples of suitable straight and branched C$_1$-C$_6$ alkyl substituents include methyl, ethyl, n-propyl, 2-propyl, n-butyl, sec-butyl, t-butyl, hexyl, and the like.

"Alkynyl" as a group or part of a group means an aliphatic hydrocarbon group containing a carbon-carbon triple bond and which may be straight or branched preferably having from 2-12 carbon atoms, more preferably 2-10 carbon atoms, more preferably 2-6 carbon atoms in the normal chain. Exemplary structures include, but are not limited to, ethynyl and propynyl.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$ cycloalkyl or $C_{5-7}$ cycloalkenyl group are fused together to form a cyclic structure, such as tetrahydronaphthyl, indenyl or indanyl. Typically an aryl group is a $C_6$-$C_{18}$ aryl group.

"Cycloalkyl" refers to a saturated monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. A cycloalkyl group typically is a $C_3$-$C_9$ cycloalkyl group.

"Halogen" represents chlorine, fluorine, bromine or iodine.

"Heteroalkyl" refers to a straight- or branched-chain alkyl group preferably having from 2 to 12 carbons, more preferably 2 to 6 carbons in the chain, in which one or more of the carbon atoms (and any associated hydrogen atoms) are each independently replaced by a heteroatomic group selected from S, O, P and NR' where R' is selected from the group consisting of H, optionally substituted $C_1$-$C_{12}$alkyl, optionally substituted $C_3$-$C_{12}$cycloalkyl, optionally substituted $C_6$-$C_{18}$aryl, and optionally substituted $C_1$-$C_{18}$heteroaryl. Exemplary heteroalkyls include alkyl ethers, secondary and tertiary alkyl amines, amides, alkyl sulfides, and the like. Examples of heteroalkyl also include hydroxy$C_1$-$C_6$alkyl, $C_1$-$C_6$alkyloxy$C_1$-$C_6$alkyl, amino$C_1$-$C_6$alkyl, $C_1$-$C_6$alkylamino$C_1$-$C_6$alkyl, and di($C_1$-$C_6$alkyl)amino$C_1$-$C_6$alkyl "Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl, 1-, 2-, or 3-indolyl, and 2-, or 3-thienyl. A heteroaryl group is typically a $C_1$-$C_{18}$ heteroaryl group.

As used herein, the term "$C_1$-$C_{12}$ alkylene" refers to a bivalent straight or branched chain aliphatic hydrocarbon group, where the group has 1 to 12 carbon atoms in the chain.

In an embodiment, X is an optionally substituted $C_1$-$C_{12}$ alkyl.

In an embodiment, X is $C_1$-$C_{12}$ alkyl.

In an embodiment, X is an optionally substituted $C_1$-$C_3$ alkyl.

In an embodiment, X is $C_1$-$C_3$ alkyl.

In an embodiment, X is methyl.

In an embodiment, X is $CH_3$.

In an embodiment, X is an optionally substituted amino, for example —$NCH_3$.

In an embodiment, X is amino.

In an embodiment, X is an optionally substituted amide. As used herein, the term "amide" refers to a functional group consisting of a carbonyl group attached to a nitrogen atom. Therefore, the term "optionally substituted amide" refers to an amide functional group that bears further substitution.

In an embodiment, X is an optionally substituted amide, for example,

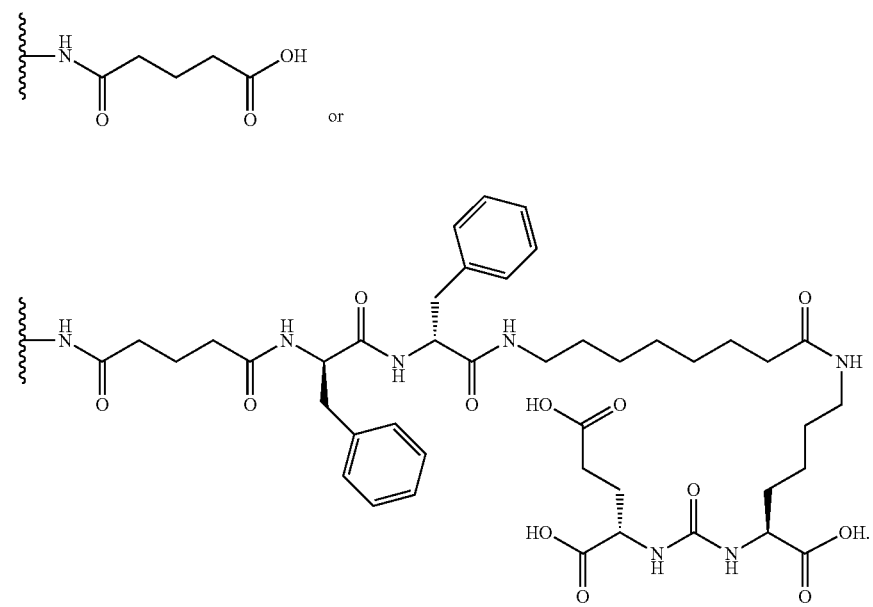

In an embodiment, Y is a substituted alkylene group.

In an embodiment, Y is an unsubstituted alkylene group.

In an embodiment, Y is $CH_2$.

In an embodiment, Y is a carbonyl group.

In an embodiment, Y is a substituted $C_1$-$C_{12}$ alkylene group, wherein one or more of the methylene groups is further substituted with an amido group, for example,

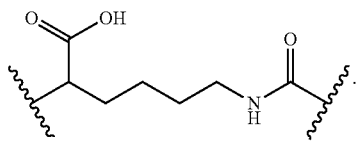 [SMILES: *C(=O)NCCCCC(*)C(=O)O]

In an embodiment, n is 1.
In an embodiment, n is 2.
In an embodiment, n is 0.
In an embodiment, m is 1.
In an embodiment, m is 2.
In an embodiment, m is 0.
In an embodiment, the present invention provides a compound of formula:

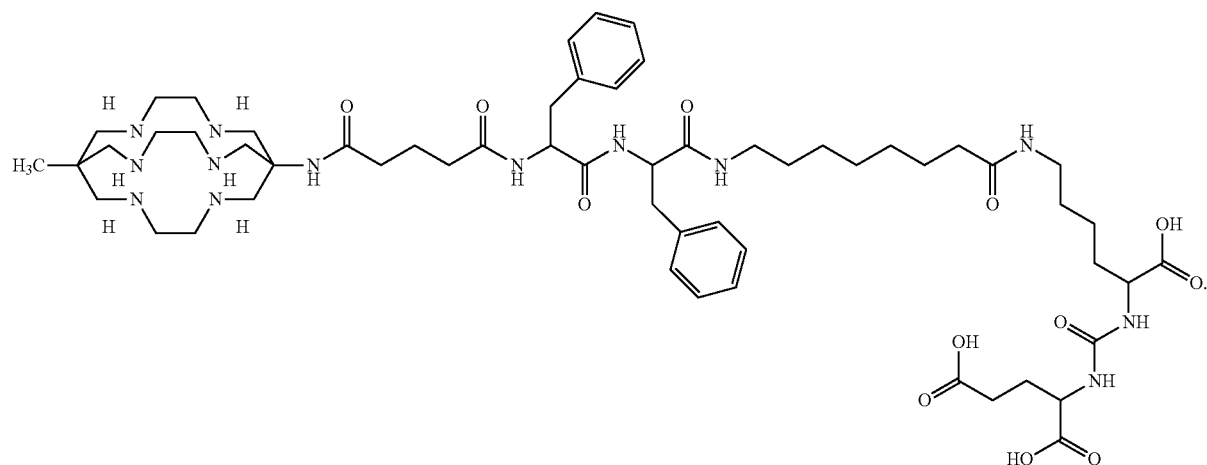

In another embodiment, the present invention provides a compound of formula:

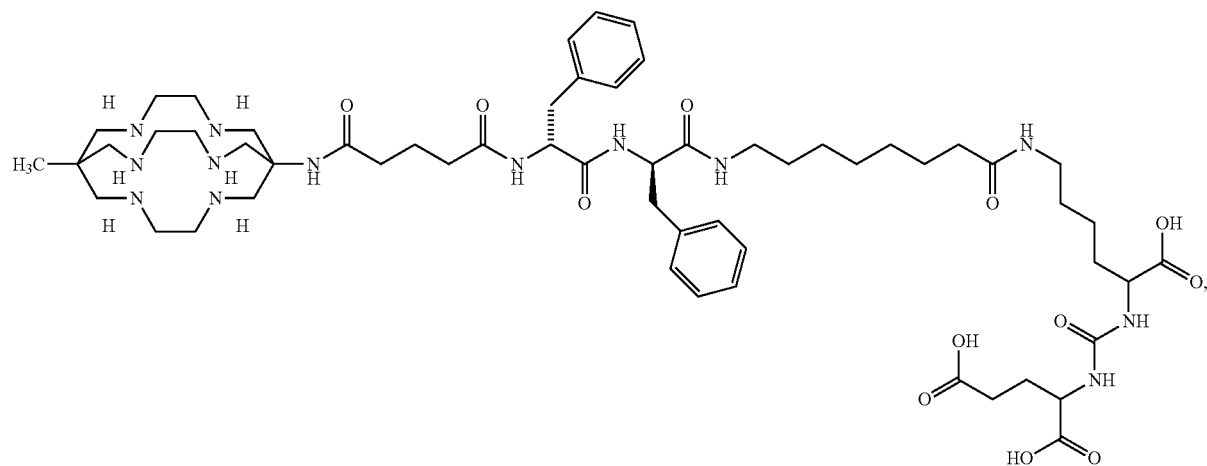

where the two phenylalanine residues are D-Phe, to give a MeCOSar-D-Phe-D-Phe-AOC-Lys-urea-Glu ligand. The inventors have identified that the use of phenylalanine residues with specifically D-stereochemistry may give rise to compounds with improved metabolic stability. Additionally, the inventors have also identified that the use of two D-Phe residues in the ligand may increase the hydrophobicity of the compounds and potential pi-pi interactions of the ligand with the binding pocket of the target enzyme.

In another embodiment, the present invention provides a compound of formula

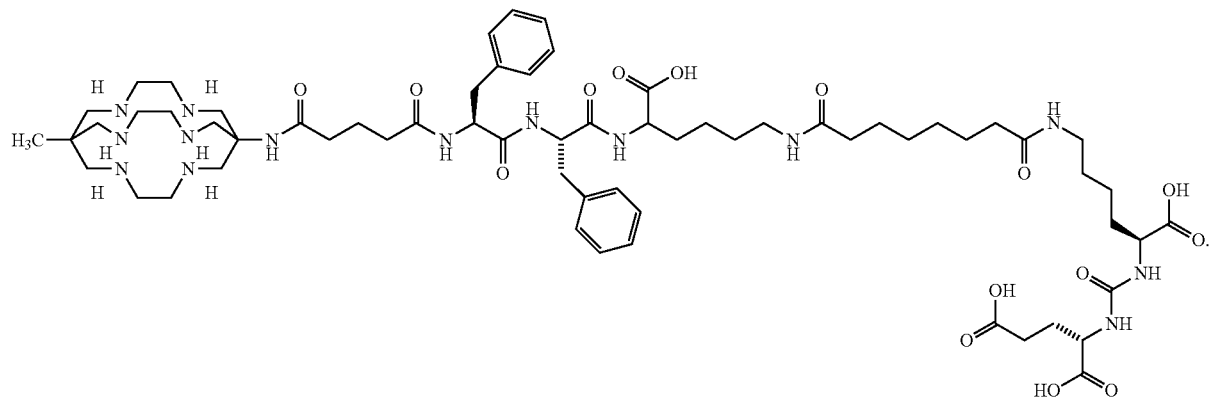

In another embodiment, the present invention provides a compound of formula:

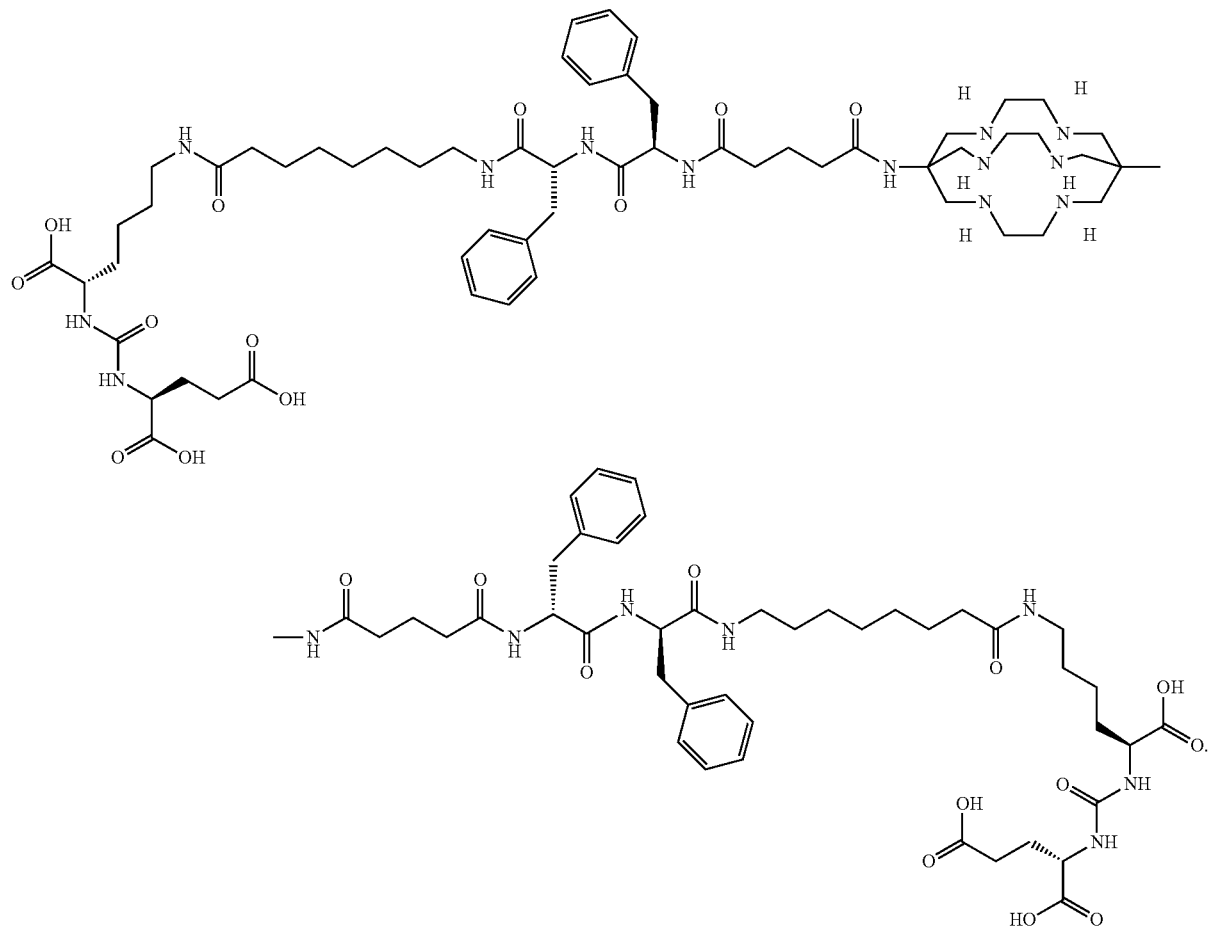

This compound comprises two linkers and two urea motifs for binding to PSMA. Without wishing to be bound by theory, it would appear that this compound bearing two urea motifs may show further improved binding affinity to PSMA. It is also thought that this bis derivative, i.e. compound with two linkers and two urea motifs, may provide a better signal to noise ratio when used for imaging purposes and as compared to the corresponding mono compound with a single linker and urea motif. The bis compound may also show a further improvement in clearance from the kidneys when administered. This may be attributed to the difference in overall charge and charge separation and distribution, when the mono and bis compounds are compared.

In another embodiment, the present invention provides a compound of formula:

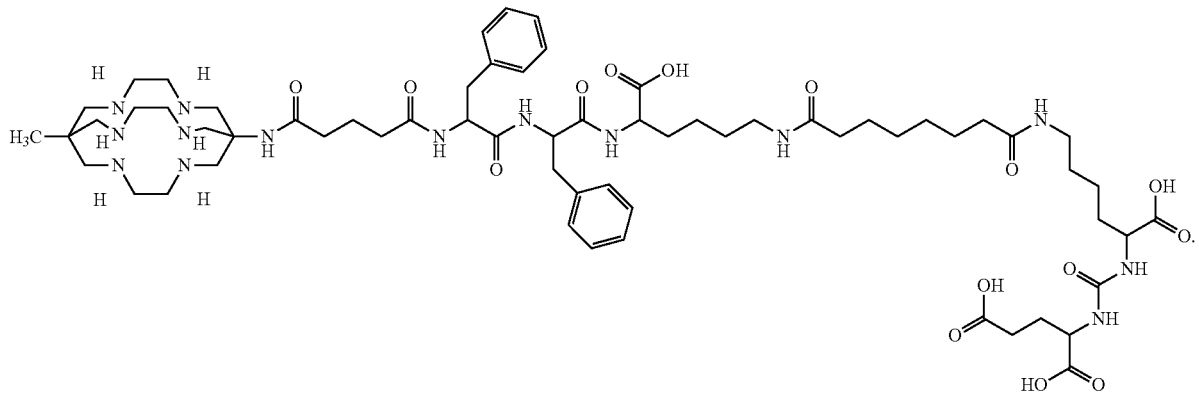

In another embodiment, the present invention provides a compound of formula:

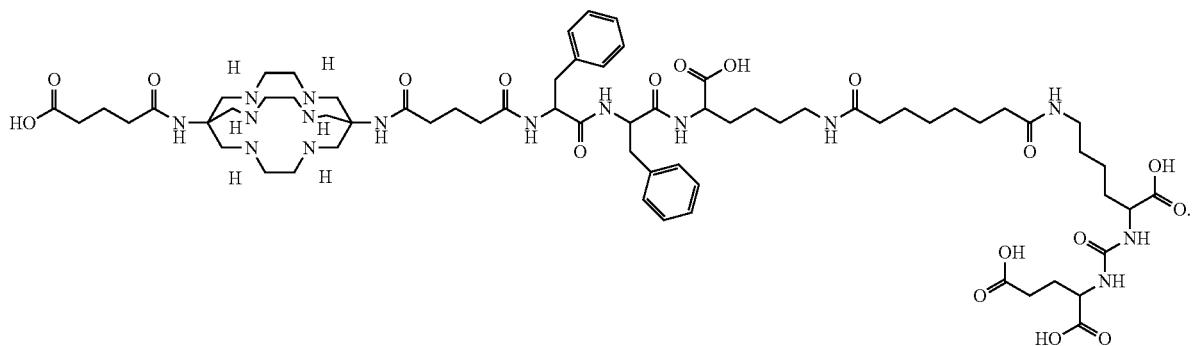

In another embodiment, the present invention provides a compound of formula:

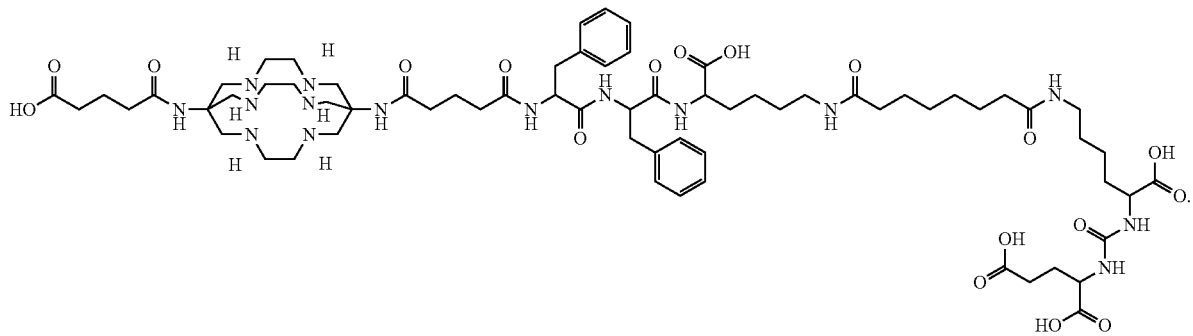

In an embodiment, the compound is coordinated with a metal ion.

In an embodiment, the metal ion is an ion of Cu, Tc, Gd, Ga, In, Co, Re, Fe, Au, Mg, Ca, Ag, Rh, Pt, Bi, Cr, W, Ni, V, Ir, Zn, Cd, Mn, Ru, Pd, Hg, Ti, Lu, Sc, Zr, Pb, Ac and Y.

In an embodiment, the metal ion is a radionuclide.

In some embodiments, the metal in the metal ion is a radionuclide selected from the group consisting of Cu, Tc, Ga, Co, In, Fe, and Ti. The present compounds have been found to be particularly applicable useful in binding copper ions. In some embodiments the metal in the metal ion is a radionuclide selected from the group consisting of $^{60}$Cu, $^{61}$Cu, $^{62}$Cu, $^{64}$Cu and $^{67}$Cu. In some embodiments the metal in the metal ion is $^{60}$Cu. In some embodiments the metal in the metal ion is $^{61}$Cu. In some embodiments the metal in the metal ion is $^{62}$Cu. In some embodiments the metal in the metal ion is $^{64}$Cu. In some embodiments the metal in the metal ion is $^{67}$Cu.

The compound of Formula (I) comprises a sarcophagine macrocyclic ligand and a Lys-urea-Glu moiety that targets PSMA. The compound also comprises intervening parts that link the sarcophagine and PSMA-targeting moiety. In Formula (I), these include a propyl linker bound by two amide groups, two phenylalanine residues and an aminooctanoic acid (AOC) group. The propyl linker, phenylalanine residues and aminooctanoic acid group together act as a spacer group to separate the sarcophagine and PSMA-targeting moiety. It is desirable that there is a degree of separation between the sarcophagine and the PSMA-targeting moiety, so as to ensure that the activity of these two groups do not interfere with each other, however it is also important that these two groups are not so far apart, such that where the sarcophagine contains a bound radionuclide, the radionuclide complex is delivered to the site of action identified by the PSMA-targeting moiety. The PSMA targeting moiety comprises a Lys-urea-Glu moiety, which has three carboxy functional groups that provide an overall negative charge and contribute to a zinc binding region. The aminooctanoic acid group adjacent to the PSMA targeting moiety is designed to provide a linker group of approximately 20 Å in length in order to separate the charge between the PSMA targeting moiety and the remainder of the molecule. The two D-phenylalanine residues are hydrophobic in nature and allow for pi-pi binding interactions with the active site. These residues also contribute to the metabolic stability of the compound. The propylene group situated between two amide functional groups also serve to provide the requisite distance between the macrocyclic ligand (which chelates a positively charged Cu ion) and the PSMA targeting moiety. The present inventors have found that the compounds according to the present invention comprise various fragments (i.e. macrocyclic ligand, linkers and PSMA targeting moiety), which together provide a PSMA-binding ligand with the requisite stability and binding affinity.

In an embodiment, the invention provides compositions comprising a compound as described above together with a pharmaceutically acceptable excipient.

In a further aspect, the invention provides a method of treating or preventing a condition in a subject in need thereof, the method comprising administering a therapeutically effective amount of a compound as described above or a composition thereof.

In an embodiment, the condition is cancer.

In an embodiment, the condition is breast cancer, colon cancer, lung cancer, ovarian cancer, prostate cancer, head and/or neck cancer, or renal, gastric, pancreatic cancer, brain cancer a hematologic malignancy such as lymphoma or leukaemia In an embodiment, the condition is prostate cancer.

In a further aspect the invention provides a method of radioimaging a subject, the method comprising administering an effective amount of a compound as described above or a composition thereof.

Ideally, a radiopharmaceutical is retained at the intended target and not at any other sites, and any unbound radiopharmaceutical cleared from the circulatory system. This would then allow for images with sufficient contrast to be obtained, which then in turn allows for a more accurate analysis and diagnosis to be performed. For this to occur, the radiolabelled complex should have physical and chemical properties where the bound complex remains bound at the desired site for a time sufficient for the requisite imaging, however any unbound complex should be cleared sufficiently from the subject to prevent any background radiation arising from the unbound complex to interfere and reduce the contrast of the images obtained.

Figure 2:
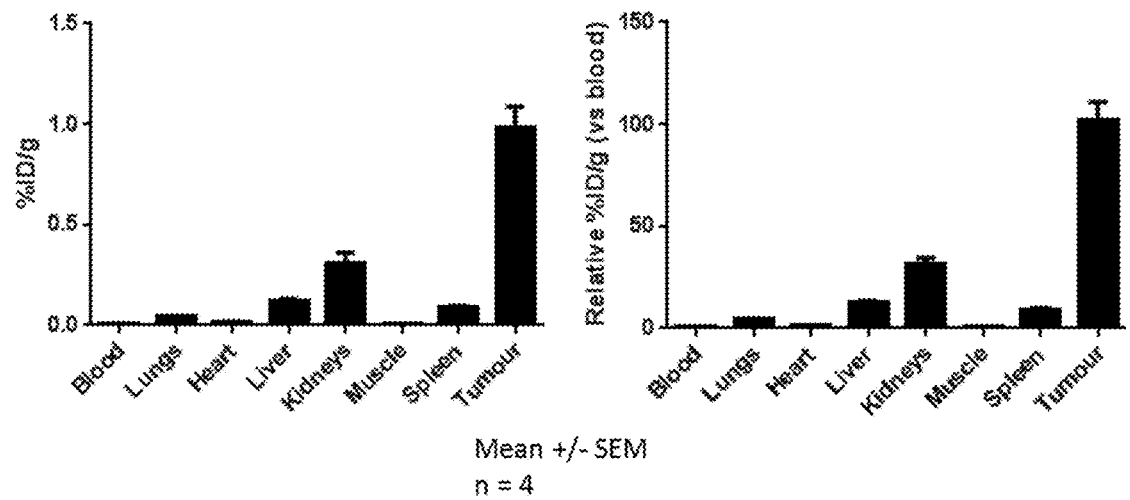
FIG. 2: Graph showing biodistribution of $^{64}$Cu-Sar-PSMA in LNCaPs bearing NSG mice (left), relative to levels in blood (right), both at 22 hours.
Figure 3:
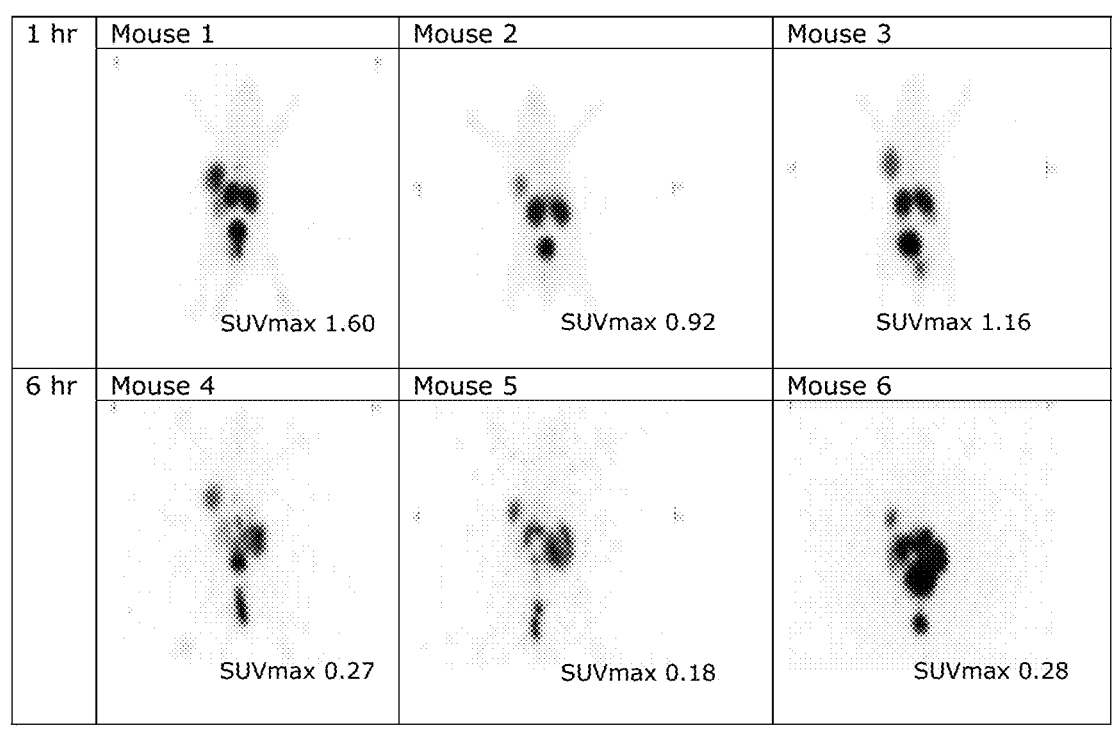
FIG. 3: PET imaging of LNCaPs bearing NSG mice treated with $^{64}$Cu-Sar-PSMA at 1 and 6 hours.
Figure 4:
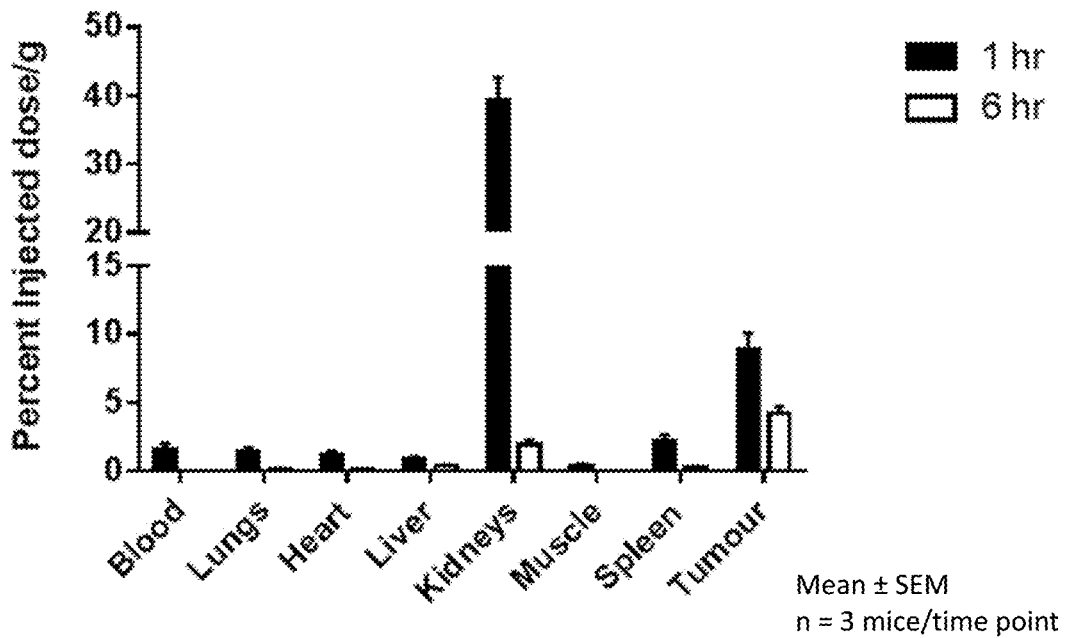
FIG. 4: Graph showing biodistribution of $^{64}$Cu-Sar-PSMA in LNCaPs bearing NSG mice at 1 and 6 hours.

The compounds of the present invention show a more favourable distribution profile in vivo. FIGS. 2 and 4 show that the administration of $^{64}$Cu-Sar-PSMA to tumour-bearing mice leads to the localisation of the compound in the tumour, rather than in any major organs or blood. Minimising binding of the radiolabelled complex to other tissues reduces the damage to healthy tissue. The complex shows relatively little accumulation in the bloodstream, which also shows the high binding affinity of the Sar-PSMA complex to tumours that express PSMA.

Figure 5:
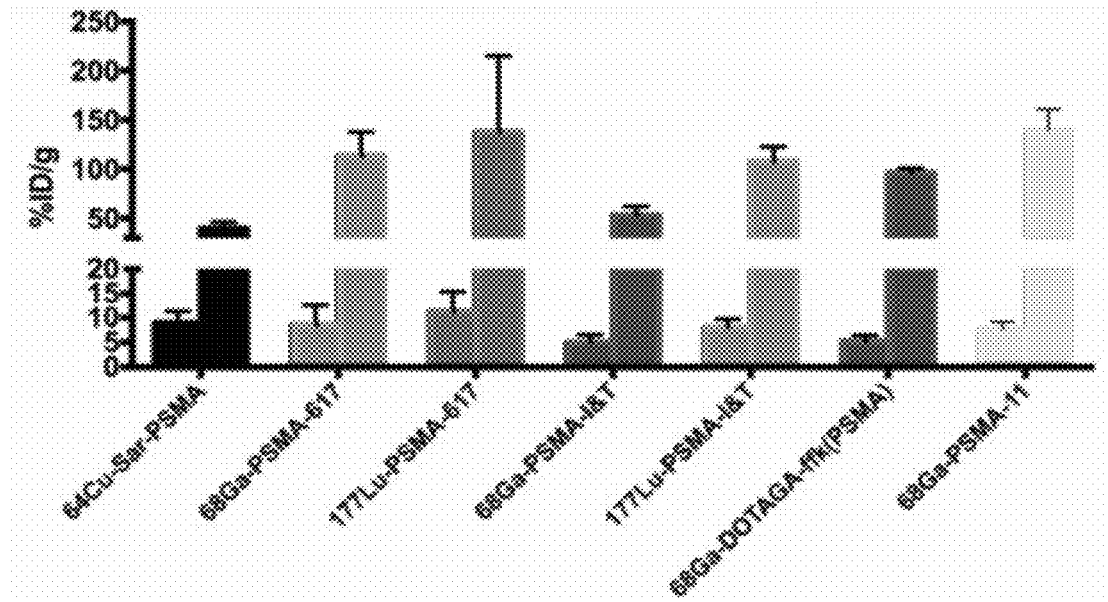
FIG. 5: Graph showing biodistribution of various radiolabelled complexes in LNCaPs xenograft mice, expressed as a ratio of uptake in tumor:kidney at 1 hour.
Figure 6:
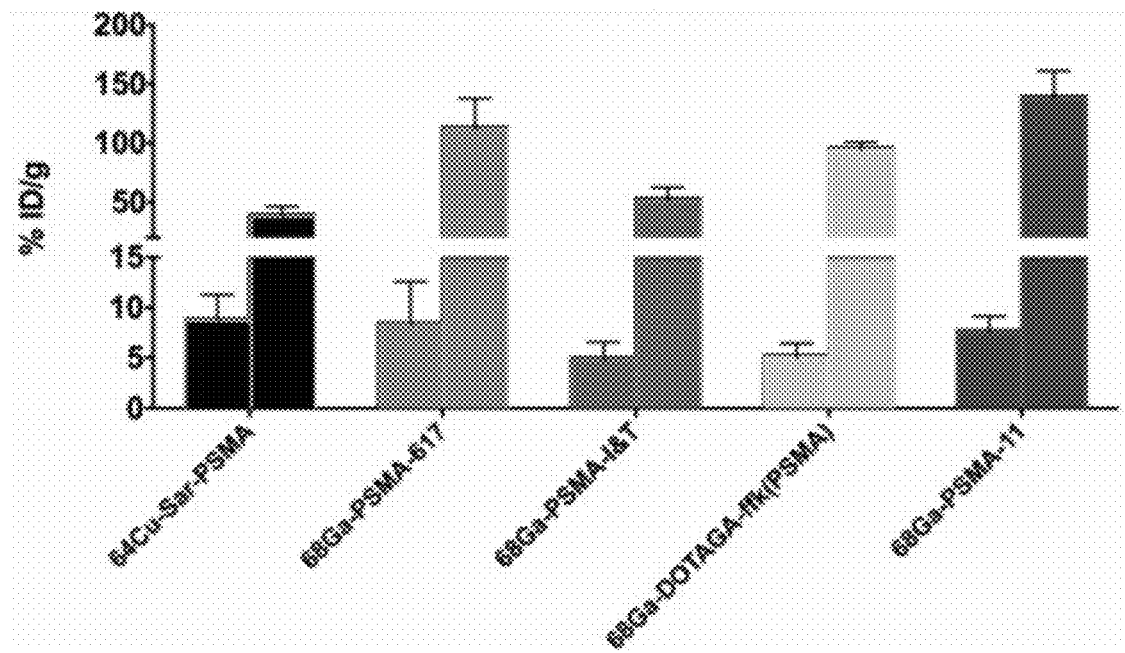
FIG. 6: Graph showing preclinical biodistribution of $^{64}$Cu-Sar-PSMA and $^{68}$Ga-labelled complexes in LNCaPs xenograft mice, expressed as a ratio of uptake in tumor:kidney at 1 hour.

In comparison with other known radiolabelled complexes (see FIG. 5), such as 68Ga-PSMA-617, $^{177}$Lu-PSMA-I&T and $^{68}$Ga-DOTAGA-ffk(PSMA), the $^{64}$Cu-Sar-PSMA complex shows greater uptake in tumours. Additionally, when uptake into the kidneys is considered, which signifies excretion of the compound, $^{64}$Cu-Sar-PSMA shows markedly less uptake into the kidneys when compared to other compounds that show similar binding to the tumour site. A similar comparison between the $^{64}$Cu-Sar-PSMA complex and various $^{68}$Ga complexes is shown in FIG. 6, which shows that the use of a $^{64}$Cu radionuclide binds to the tumour as well, or better than, the complexes that use a $^{68}$Ga radionuclide. Furthermore, the $^{64}$Cu-Sar-PSMA complex shows less uptake into the kidneys than the complexes with a $^{68}$Ga radionuclide.

Subsequently, the present inventors have found that the use of the Sar-PSMA ligand and a $^{64}$Cu radionuclide shows better affinity for the tumour site and better clearance from the kidneys after administration. These advantages allow for better imaging results to be obtained, i.e. higher affinity for the tumour site provides images with better contrast, as the radionuclide is predominantly located at the target site and better removal of unbound ligand from the circulation, thereby reducing background accumulation. This then allows for improved diagnosis of tumours such as prostate cancer. The increased affinity for the tumour binding site also suggests that there is less diffusion of the radionuclide to other tissues, which improves the quality of the images obtained. Furthermore, minimising the diffusion of the radionuclide to areas that are not the tumour site means that less of the radiolabelled complex is required for administration and that any detrimental effects from the radioactive complex is localised, such that healthy tissue is not affected.

The inventors have found that the present compounds may be used as theranostic compounds. The theranostic approach allows for the same compound to be used in the diagnosis and treatment of an indication, which provides advantages over the use of one compound for diagnosis and a different compound for treatment. Overall, this allows for greater efficiency in diagnosis and treatment of a particular disease. This is in contrast to traditional methods, where a ligand with a particular isotope may be suitable for diagnosing a disease, however the same combination of ligand and isotope may not be suitable for treating the disease. This then requires that the ligand, the isotope or both the ligand and isotope are modified in order to treat the disease.

Figure 7:
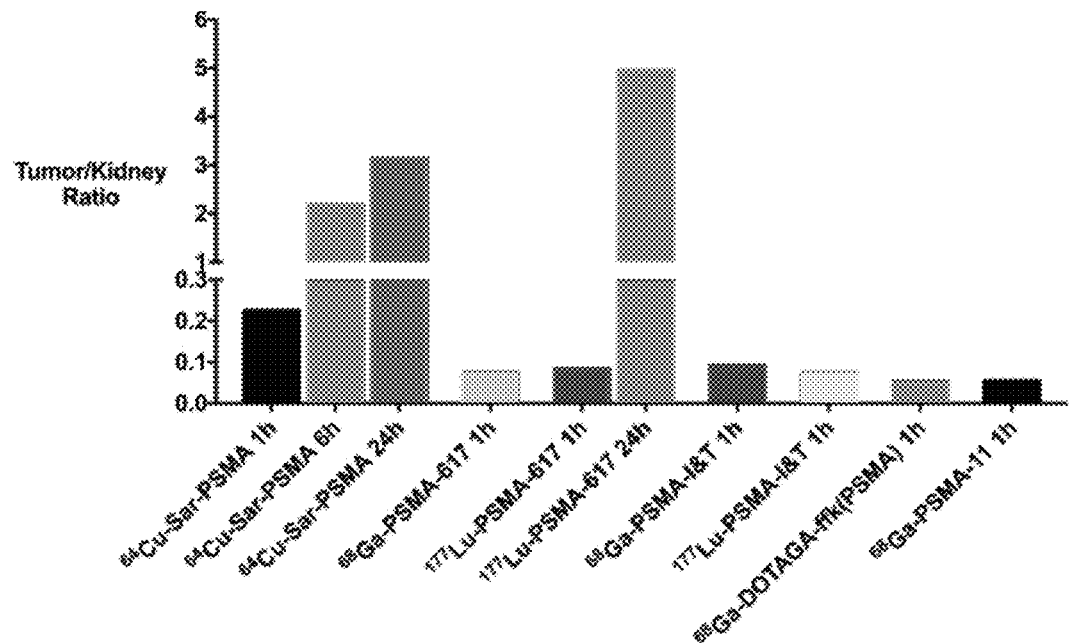
FIG. 7: Graph showing biodistribution of various radiolabelled complexes in LNCaPs xenograft mice, expressed as a ratio of uptake in tumor:kidney.
Figure 8:
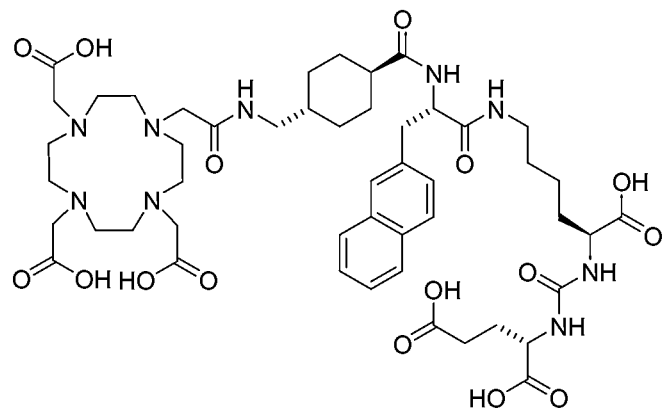
FIG. 8: Structures of PSMA ligand targets of the prior art.
Figure 8:
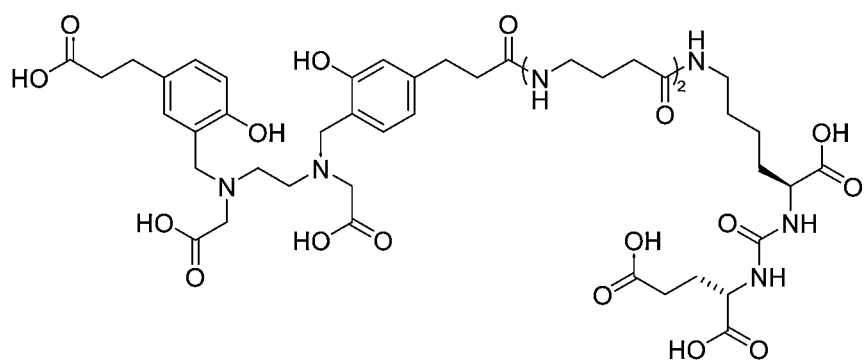
Figure 8:
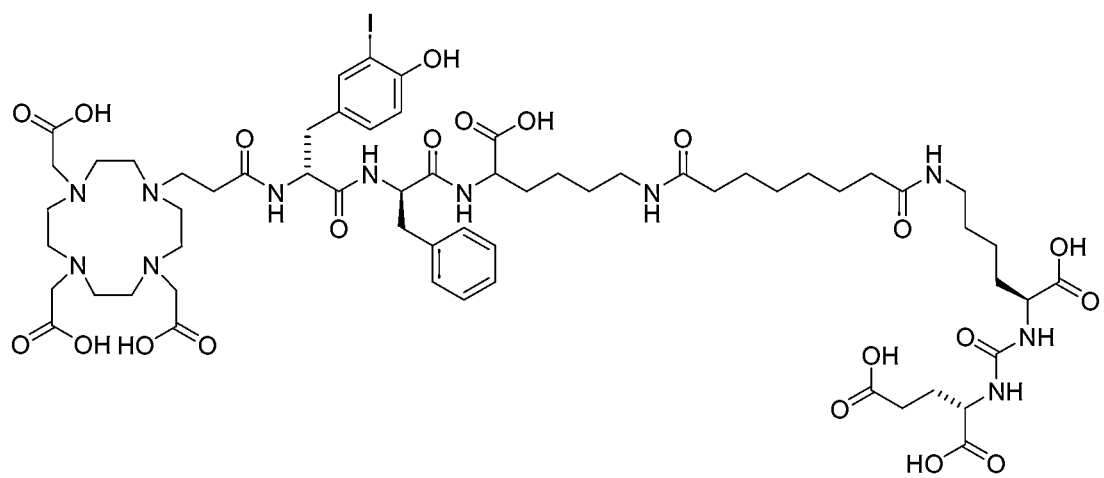
Figure 9:
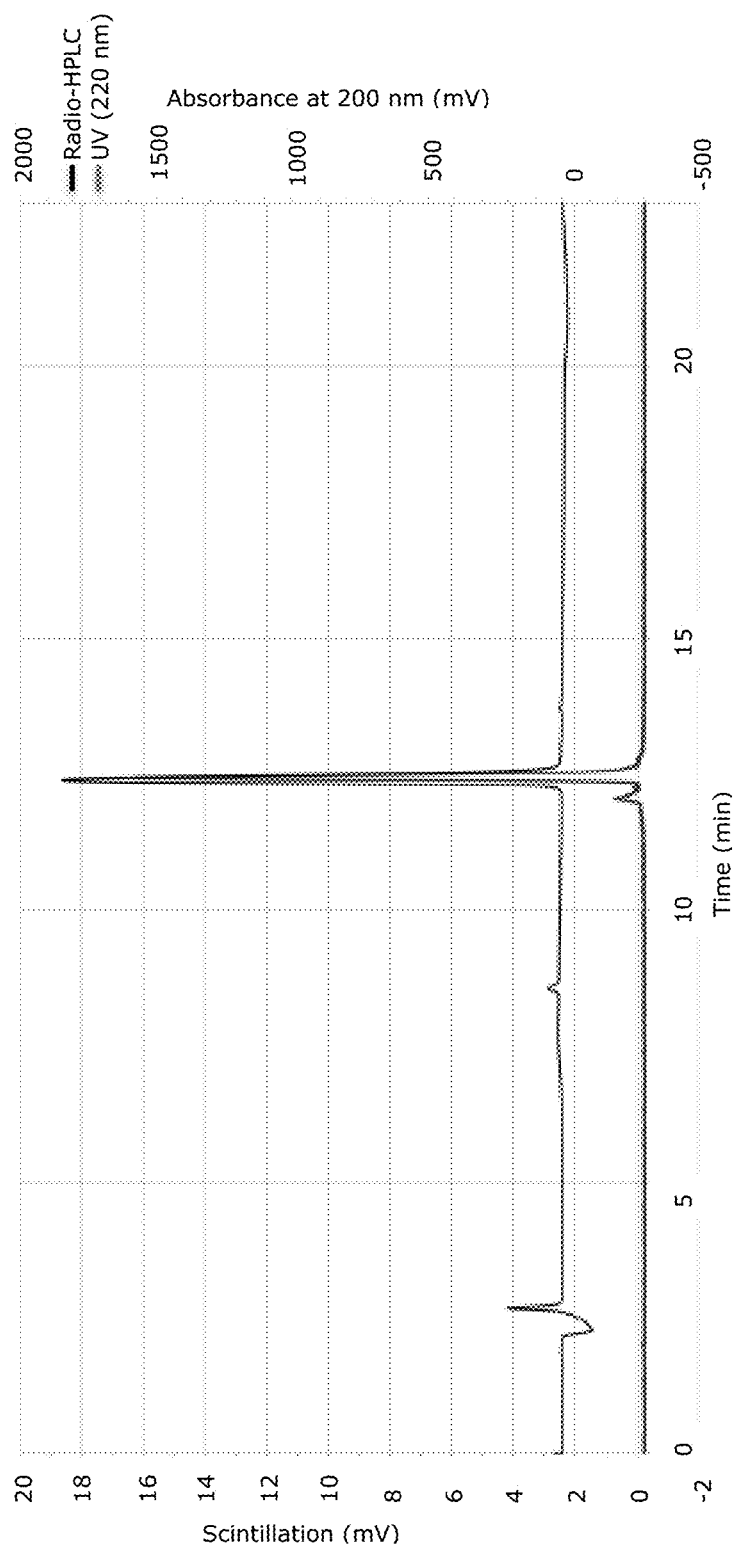
FIG. 9: HPLC chromatogram of $^{64}$Cu-Sar-PSMA (R$_T$: 12.43 min) compared to $^{nat}$Cu-Sar-PSMA (R$_T$: 12.38 min) with UV detection at 220 nm.
Figure 10:
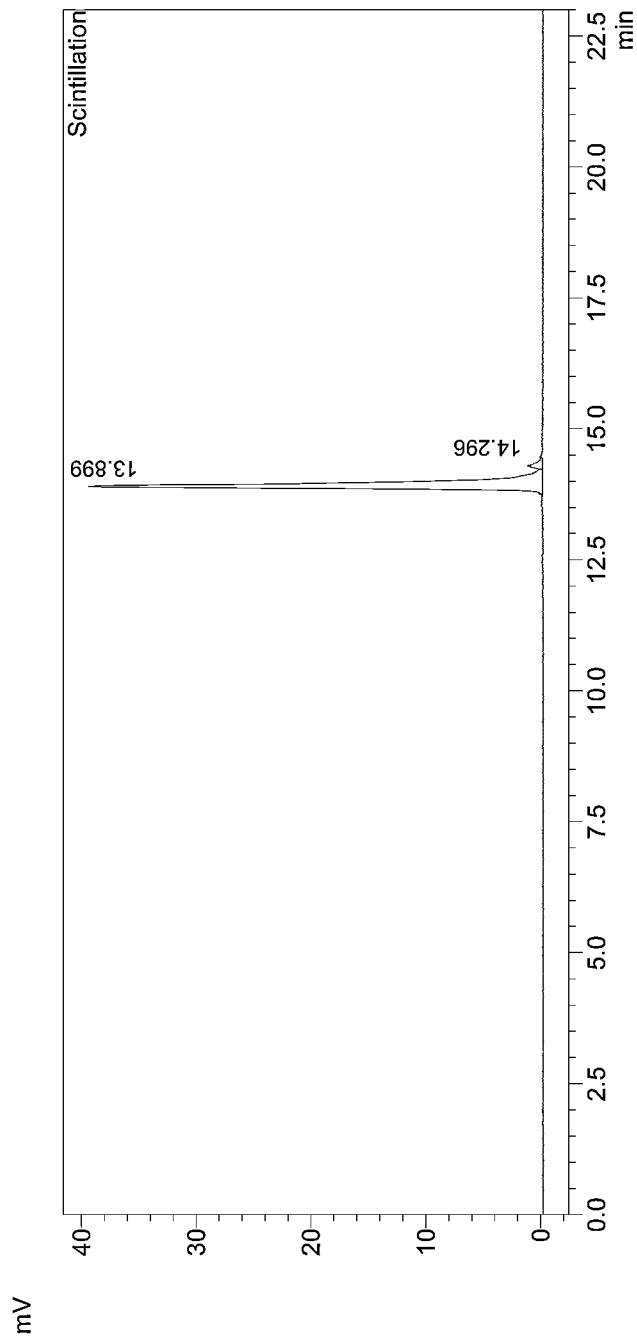
FIG. 10: Radio-HPLC chromatogram of $^{64}$Cu-CoSar (PSMA)$_2$ (R$_T$: 13.9 min).
Figure 11:
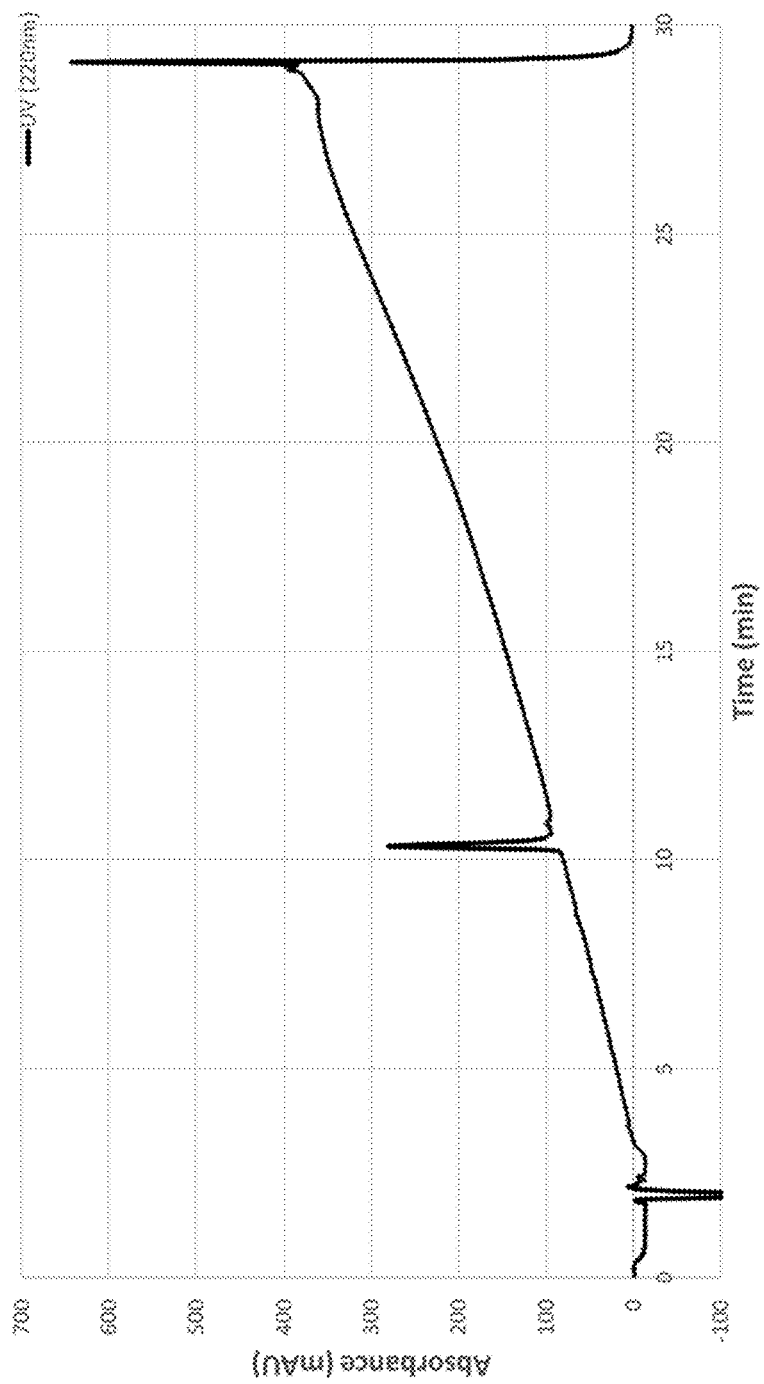
FIG. 11: Analytical HPLC chromatogram of CoSar (PSMA)$_2$ (R$_T$: 10.3 min) with UV detection at 220 nm.

FIG. 7 shows the accumulation of radiolabelled complexes in tumours and the kidney over time. Where the $^{64}$Cu-Sar-PSMA complex is administered, the ratio of the complex located in the tumour to the complex located in the tumour increases up to a time of 24 hours. FIG. 7 shows that the uptake of the $^{64}$Cu-Sar-PSMA complex in tumour sites after 1 hour is greater than the other radiolabelled complexes, which indicates that the $^{64}$Cu-Sar-PSMA complex is taken up faster than the other comparator complexes. Furthermore, the ratio of the complex in tumours to the kidney increases up to a time of 24 hours, which then indicates that the complex has a favourable binding affinity to the tumour. The advantages arising from this is that as the complex remains bound for a longer period of time, imaging of the subject can be performed over this time period to allow for images of better quality and higher contrast can be obtained. This then allows for a more accurate diagnosis of the disease to be made.

The $^{64}$Cu-Sar-PSMA complex shows improved binding affinity over other radiolabelled complexes, which also indicates that the same complex may be of use for therapy. As the therapeutic nature of the complex relies on the delivery of the radionuclide to the target site, i.e. the tumour, good specificity and affinity for the tumour site is necessary. This allows for the radionuclide to deliver the radiotherapeutic effect to the desired site and prevent damage to other tissues. Furthermore, the ability of the radiolabelled complex to remain bound to the target site allows for a prolonged therapeutic effect to be delivered, which increases the efficiency of the method of treatment.

The present inventors have now shown that the $^{64}$Cu-Sar-PSMA radiolabelled complex has sufficient binding specificity and affinity for the target PSMA site, such that administration of a therapeutically effective amount of the radiolabelled complex may allow for the treatment of prostate cancer.

The present inventors have also now shown that the Sar-PSMA complex radiolabelled with a copper isotope may be used for both diagnostic and therapeutic purposes. For example, the $^{64}$Cu-Sar-PSMA radiolabelled complex may be used for both diagnostic and therapeutic purposes. The $^{67}$Cu-Sar-PSMA radiolabelled complex may also be used for both diagnostic and therapeutic purposes.

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic and arylsulfonic. Additional information on pharmaceutically acceptable salts can be found in Remington's Pharmaceutical Sciences, 19th Edition, Mack Publishing Co., Easton, PA 1995. In the case of agents that are solids, it is understood by those skilled in the art that the inventive compounds, agents and salts may exist in different crystalline or polymorphic forms, all of which are intended to be within the scope of the present invention and specified formulae.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state. An effective amount for radioimaging is typically sufficient to identify the radionuclide in the subject.

The monitoring of the subject for the location of the radiolabelled material will typically provide the analyst with information regarding the location of the radiolabelled material and hence the location of any material that is targeted by the molecular recognition moiety (such as cancerous tissue). An effective amount of the compounds of the invention will depend upon a number of factors and will of necessity involve a balance between the amount of radioactivity required to achieve the desired radio imaging effect and the general interest in not exposing the subject (or their tissues or organs) to any unnecessary levels of radiation which may be harmful.

The methods of treatment of the present invention involve administration of a compound of formula (I) which has been complexed to a radionuclide. The compounds of formula (I) are able to deliver the radionuclide to the desired location in the body where its mode of action is desired.

A therapeutically effective amount can be readily determined by an attending clinician by the use of conventional techniques and by observing results obtained under analogous circumstances. In determining the therapeutically effective amount a number of factors are to be considered including but not limited to, the species of animal, its size, age and general health, the specific condition involved, the severity of the condition, the response of the patient to treatment, the particular radio labelled compound administered, the mode of administration, the bioavailability of the preparation administered, the dose regime selected, the use of other medications and other relevant circumstances.

In addition the treatment regime will typically involve a number of cycles of radiation treatment with the cycles being continued until such time as the condition has been ameliorated. Once again the optimal number of cycles and the spacing between each treatment cycle will depend upon a number of factors such as the severity of the condition being treated, the health (or lack thereof) of the subject being treated and their reaction to radiotherapy. In general the optimal dosage amount and the optimal treatment regime can be readily determined by a skilled addressee in the art using well known techniques.

In using the compounds of the invention they can be administered in any form or mode which makes the compound available for the desired application (imaging or radio therapy). One skilled in the art of preparing formulations of this type can readily select the proper form and mode of administration depending upon the particular characteristics of the compound selected, the condition to be treated, the stage of the condition to be treated and other relevant circumstances. We refer the reader to Remington's Pharmaceutical Sciences, 19$^{th}$ edition, Mack Publishing Co. (1995) for further information.

The compounds of the present invention can be administered alone or in the form of a pharmaceutical composition in combination with a pharmaceutically acceptable carrier, diluent or excipient. The compounds of the invention, while effective themselves, are typically formulated and administered in the form of their pharmaceutically acceptable salts as these forms are typically more stable, more easily crystallised and have increased solubility.

The compounds are, however, typically used in the form of pharmaceutical compositions which are formulated depending on the desired mode of administration. The compositions are prepared in manners well known in the art.

The invention in other embodiments provides a pharmaceutical pack or kit comprising one or more containers filled with one or more of the ingredients of the pharmaceutical compositions of the invention. In such a pack or kit can be found at least one container having a unit dosage of the agent(s). Conveniently, in the kits, single dosages can be provided in sterile vials so that the clinician can employ the vials directly, where the vials will have the desired amount and concentration of compound and radio nucleotide which may be admixed prior to use. Associated with such container(s) can be various written materials such as instructions for use, or a notice in the form prescribed by a governmental agency regulating the manufacture, use or sale of pharmaceuticals, imaging agents or biological products, which notice reflects approval by the agency of manufacture, use or sale for human administration.

The compounds of the invention may be used or administered in combination with one or more additional drug(s) that are anti-cancer drugs and/or procedures (e.g. surgery, radiotherapy) for the treatment of the disorder/diseases mentioned. The components can be administered in the same formulation or in separate formulations. If administered in separate formulations the compounds of the invention may be administered sequentially or simultaneously with the other drug(s).

In addition to being able to be administered in combination with one or more additional drugs that include anti-cancer drugs, the compounds of the invention may be used in a combination therapy. When this is done the compounds are typically administered in combination with each other.

the like. Prolonged absorption of the injectable pharmaceutical form may be brought about by the inclusion of agents that delay absorption such as aluminium monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

In an embodiment, the present invention provides an aqueous composition of a compound of Formula (I) or a salt thereof:

(I)

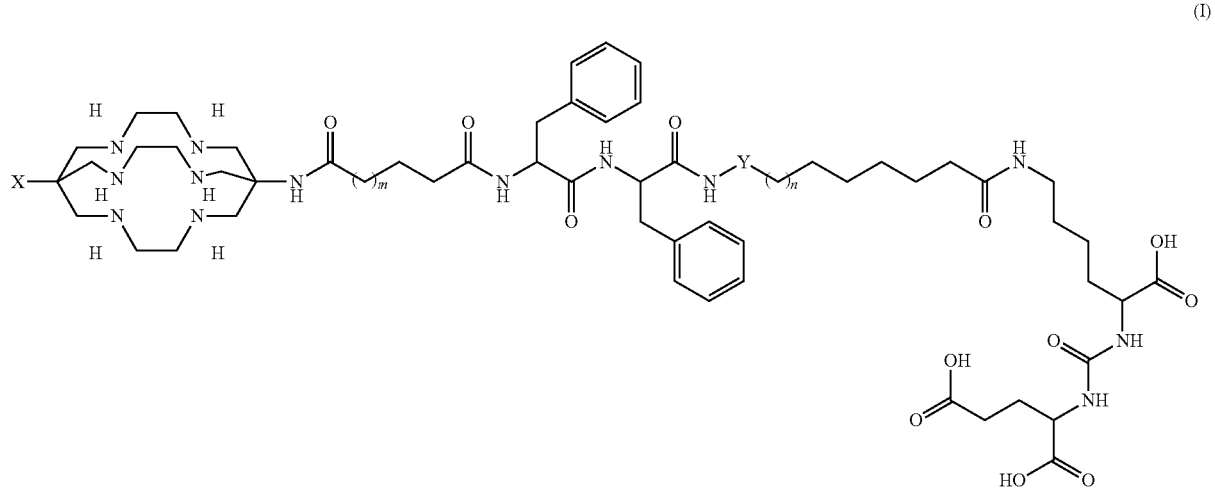

Thus one or more of the compounds of the invention may be administered either simultaneously (as a combined preparation) or sequentially in order to achieve a desired effect. This is especially desirable where the therapeutic profile of each compound is different such that the combined effect of the two drugs provides an improved therapeutic result.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and wherein:
X is a group selected from H, OH, halogen, cyano, $NO_2$, $NH_2$, optionally substituted $C_1$-$C_{12}$ alkyl, optionally substituted amino, optionally substituted amide and optionally substituted aryl;
Y is an optionally substituted $C_1$-$C_{12}$ alkylene group, wherein one or more of the methylene groups in the alkylene groups is optionally substituted for a group selected from amide, carbonyl, urea and thiourea;
m is 0, 1, or 2; and
n is 0, 1, or 2;
wherein the compound of Formula (I) is complexed with a Cu ion;
and wherein the composition further comprising ethanol, gentisic acid or a salt thereof, and sodium chloride.

The present inventors have identified that the use of gentisic acid and ethanol in a composition of the compound of Formula (I) with a complexing Cu ion may assist in preventing or minimising radiolysis of the radiolabelled complex.

In the above embodiments, the compositions of the present invention comprise ethanol as a component. The ethanol used in the composition may be anhydrous ethanol. Alternatively, the ethanol used in the composition may not have been subject to drying processes and may be hydrated. The ethanol is preferably pharmaceutical grade ethanol. The ethanol present in the composition may assist in preventing radiolysis of the radiolabelled complex of Formula (I).

In the above embodiments, the compositions of the present invention also comprise sodium chloride as a component. The sodium chloride in the formulations of the present invention may be provided as a saline solution. A saline solution is defined as an aqueous solution of sodium chloride. For example, normal saline is defined as an aqueous solution of sodium chloride at a concentration of 0.9% (w/v). In an embodiment of the present invention, the sodium chloride of a formulation is provided by a saline solution.

In the above embodiments, the compositions of the present invention comprise gentisic acid, or pharmaceutically acceptable salts and/or hydrates thereof, as a component. Gentisic acid is also known as 2,5-dihydroxybenzoic acid, 5-hydroxysalicylic acid or hydroquinonecarboxylic acid. Salts of gentisic acid may include the sodium salt and the sodium salt hydrate. Any reference to gentisic acid may include a reference to salts thereof, where relevant. It has been identified by the present inventors that the gentisic acid, or salt thereof, within the present composition may assist in preventing or minimising radiolysis of the radiolabelled complex of Formula (I).

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

If desired, and for more effective distribution, the compounds can be incorporated into slow release or targeted delivery systems such as polymer matrices, liposomes, and microspheres.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

As discussed above, the compounds of the embodiments may be useful for treating and/or detecting proliferative diseases. Examples of such cell proliferative diseases or conditions include cancer (include any metastases), psoriasis, and smooth muscle cell proliferative disorders such as restenosis. The compounds of the present invention may be particularly useful for treating and/or detecting tumours such as breast cancer, colon cancer, lung cancer, ovarian cancer, prostate cancer, head and/or neck cancer, or renal, gastric, pancreatic cancer and brain cancer as well as hematologic malignancies such as lymphoma and leukaemia. In addition, the compounds of the present invention may be useful for treating and/or detecting a proliferative disease that is refractory to the treatment and/or detecting with other anti-cancer drugs; and for treating and/or detecting hyperproliferative conditions such as leukaemia's, psoriasis and restenosis. In other embodiments, compounds of this invention can be used to treat and/or detect pre-cancer conditions or hyperplasia including familial adenomatous polyposis, colonic adenomatous polyps, myeloid dysplasia, endometrial dysplasia, endometrial hyperplasia with atypia, cervical dysplasia, vaginal intraepithelial neoplasia, benign prostatic hyperplasia, papillomas of the larynx, actinic and solar keratosis, seborrheic keratosis and keratoacanthoma.

Synthesis of Compounds of the Invention

The agents of the various embodiments may be prepared using the reaction routes and synthesis schemes as described below, employing the techniques available in the art using starting materials that are readily available. The preparation of particular compounds of the embodiments is described in detail in the following examples, but the artisan will recognize that the chemical reactions described may be readily adapted to prepare a number of other agents of the various embodiments. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions. A list of suitable protecting groups in organic synthesis can be found in T. W. Greene's Protective Groups in Organic Synthesis, $3^{rd}$ Edition, John Wiley & Sons, 1991. Alternatively, other reactions disclosed herein or known in the art will be recognized as having applicability for preparing other compounds of the various embodiments. Reagents useful for synthesizing compounds may be obtained or prepared according to techniques known in the art.

Example 1

Synthesis of Sar-PSMA

Scheme 1 outlines the route taken for the synthesis of the compound of Sar-PSMA 1.

The MeCOSar-D-Phe-D-Phe-Aoc-Lys-urea-Glu ligand 1, where Aoc=8-aminooctanoic acid (i.e. Sar-PSMA), was prepared via solid phase peptide synthesis. The glutamate-urea-lysine binding motif was synthesized by reacting an imidazole-activated and protected glutamic acid with protected L-lysine that had been immobilised on Wang resin. The peptide linker was conjugated to the ε-amine of lysine via solid-phase peptide synthesis using a standard Fmoc protocol. The conjugation of the chelator was performed by reacting $(tBoc)_{4-5}$MeCOSar with the side-chain protected linker-urea on solid support. The Sar-PSMA was cleaved from the resin and deprotected simultaneously (TFA/TIPS/$H_2O$).

Radiolabelling of Sar-PSMA with $^{64}Cu^{II}$

The Sar-PSMA ligand 1 was radiolabelled with $^{64}Cu^{II}$ at room temperature in aqueous solution (0.1 M $NH_4OAc$, pH 8, 1-10 nmol Sar-PSMA). Elution from a solid-phase cartridge (Phenomenex Strata-X RP 60 mg/mL) afforded $^{64}Cu$-Sar-PSMA in >94% yield (n.d.c.) and >97% radiochemical yield (7.95-21.9 GBq/μmol).

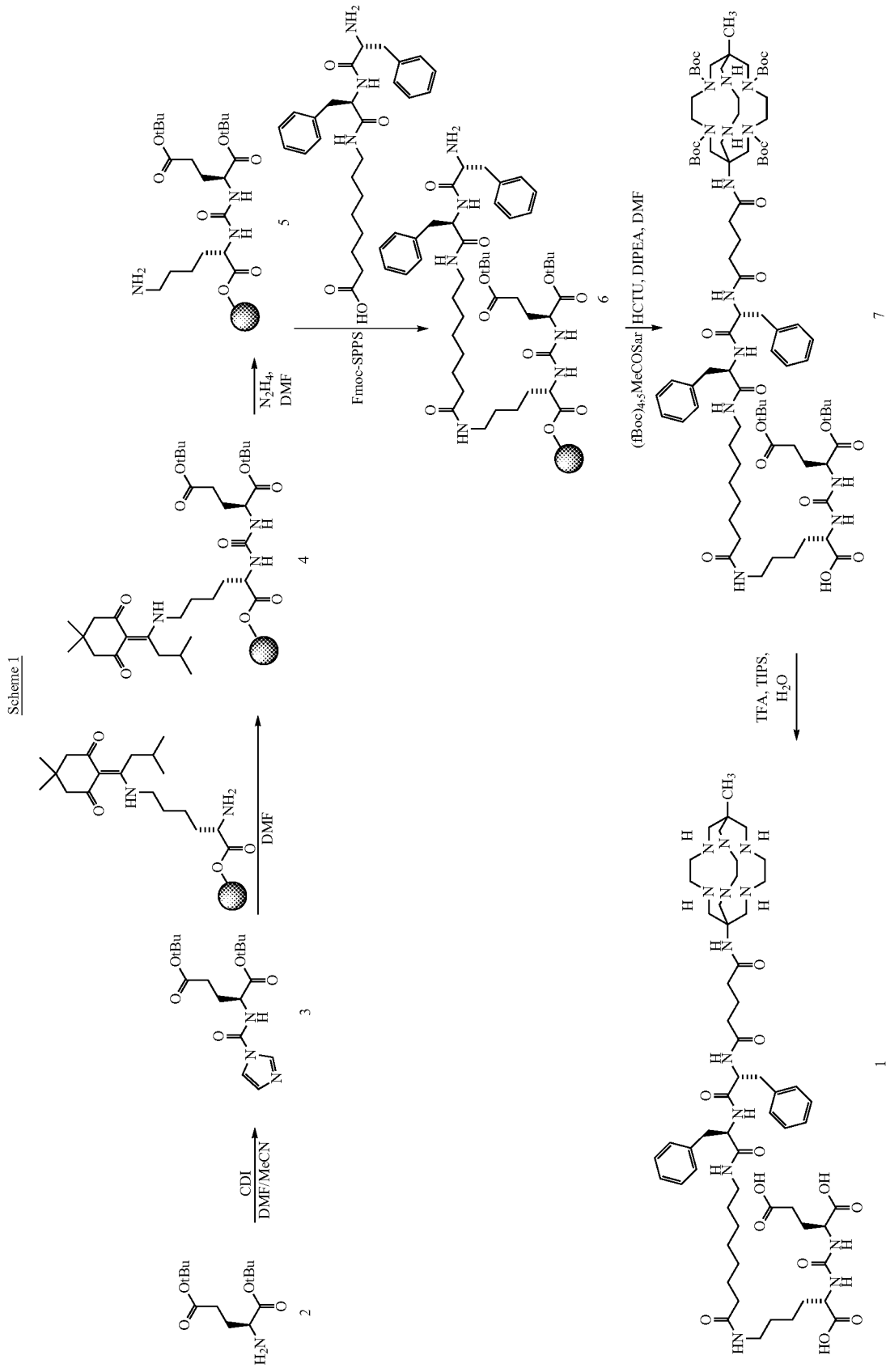

Synthesis of Activated Glu Intermediate, 3

Reference: Duspara, P. A.; Islam, M. S.; Lough, A. J.; Batey, R. A., Synthesis and reactivity of N-alkyl carbamoylimidazoles: development of N-methyl carbamoylimidazole as a methyl isocyanate equivalent. *J Org Chem* 2012, 77 (22), 10362-8.

To a flask containing L-Bis(tBu)Glu HCl 2 (3.56 g, 12.04 mmol, 1.0 eq) and carbonyl diimidazole (2.15 g, 13.24 mmol, 1.1 eq) was added a 1:5 mixture of DMF/MeCN (50 mL). The reaction was stirred overnight at RT. After stirring, the solvent was removed in vacuo and the remaining crude mixture was dissolved and purified via flash chromatography (mobile phase: 7:3:1 petroleum spirits/chloroform/methanol, $R_f$: ~0.24, 30:1 silica/crude mass ratio) to afford the product as a white semi-crystalline powder, (2.25 g, 52.9% yield).

Loading of Wang Resin with Fmoc-Lys(DDiv)-OH

To a 50 mL falcon tube containing Wang Resin (1.028 g, 1.15 mmol/g, 1.18 mmol) was added a preactivated mixture of Fmoc-Lys(DDiv)-OH (2.038 g, 3.55 mmol, 3.0 eq), HCTU (1.33 g, 3.5 mmol, 2.96 eq), DIPEA (1.24 mL, 7.09 mmol, 6 eq), DMAP (43.3 mg, 0.355 mmol, 0.3 eq) in DMF. The resin was placed on the shaker for 2 h and allowed to react. To the reaction mixture was then added acetic anhydride (223 µL, 2.36 mmol, 2 eq) and pyridine (190 µL, 2.36 mmol, 2 eq) to cap the remaining functional groups of resin and stirred for 30 min. The resin was then filtered and washed with DMF×3, DCM×3, MeOH×2, and Et₂O×2, dried, and weighed to determine the final resin loading (0.759 mmol/g). Resin loading was determined as follows:

$$\text{Resin Loading} = \frac{\text{final weight} - \text{initial weight}}{\text{MW of } Fmoc - Lys(DDiv) - \text{OH}} \text{ mmol/g}$$

Synthesis of Protected KuE on Resin, 4

The Sar-PSMA ligand was synthesised from the KuE motif on the resin under standard Fmoc solid phase peptide synthesis conditions.

General Fmoc Deprotection Protocol

The resin bound peptide 4 was treated with a solution of 20% piperidine in DMF for 5 min×3. The resin was then washed consecutively with DMF×3 and DCM×3.

TNBSA Test for Confirmation of Coupling/Deprotection Reaction

A qualitative test was carried out for each coupling/deprotection step using the TNBSA (trinitrobenzenesulfonic acid) test. A small fraction of the resin (approx. 20 beads) was placed into an Eppendorf tube. TNBSA (10 µL of 5% solution in DMF) and DIPEA (10 µL of 5% solution in DMF) were added and the mixture was agitated for 2 min. If no color change of the resin was observed, the test was indicative of an absence of a primary amine, whilst an orange color of the resin was indicative of the presence of a free primary amine.

After deprotection, a solution of the activated Glu intermediate 3 (0.95 g, 2.69 mmol, 2.0 eq) and DIPEA (240 µL, 1.38 mmol, 1.0 eq) in DMF (5 mL) was added to the resin. The resin was stirred manually over 24 h and washed with DMF×3 and DCM×3. After confirmation of coupling via TNBSA and test cleavage/MS, the DDiv group was deprotected by treatment with 2% hydrazine hydrate in DMF×3 to give 5.

General Protocol for Coupling Fmoc-Amino Acid to Resin

Fmoc amino acid (3 equiv.) was activated using HCTU (0.96 eq relative to AA) and DIPEA (2 eq relative to AA) in DMF. After 5 min, the solution was added onto the resin and was occasionally stirred. After 20 min, the resin was filtered and washed consecutively with DMF×1, DCM×3, and DMF×3 to give 6.

Coupling of MeCOSar onto PSMA Ligand on Resin to give 7

BocMeCOSar (0.464 g, 0.5 mmol, 1.2 eq) was activated using HCTU (0.207 g), HOBt (67.6 mg), and DIPEA (174 µL) in DMF. After 5 min, the solution was added to the resin 6 (0.4 mmol) and occasionally stirred. After 24 h, the resin was filtered and washed consecutively with DMF×1, DCM×3, and DMF×3.

Resin Cleavage Protocol to produce 1 The resin 7 was washed several times with DCM and then transferred to a 50 mL falcon tube. 95:2.5:2.5 TFA/TIPS/H₂O (15 mL) was added and the resin was agitated at rt for 2 h. The resin was filtered and washed twice with 3 mL TFA. The filtrate was collected and the TFA was evaporated under a stream of N₂. The crude peptide was precipitated by addition of excess chilled Et₂O and centrifuged. The Et₂O was decanted and the process was repeated ×3. The precipitated crude peptide was dried and weighed and purified via prep-HPLC.

HPLC Purification

The crude peptide (818 mg) was reconstituted in 22% MeCN in H₂O (6.4 mL) and purified in portions by RP-HPLC (24% isocratic for 60 min) on a Kinetex 5 µ 100 Å AXIA-packed C18 21.2×150 mm semi-preparative column at 5 mL/min. The fractions containing the product were separated and lyophilized to afford the product 1 as a fluffy white powder (58.5 mg, 16.1% based on resin used).

Radiolabeling

An aliquot of $^{64}Cu^{II}$ (30-200 MBq, 0.1 M NH₄OAc, pH 6) was added to a solution containing Sar-PSMA 1 (5 µg, 4.3×10⁻³ µmol) in MilliQ water, NH₄OAc, pH 5 (final concentration: 0.05M), ethanol (10%), and gentisic acid in MilliQ water (final concentration: 0.056%) and the pH was measured (pH: 5). The reaction was incubated for 30 min at room temperature. After 30 minutes, an aliquot was analysed by RP-HPLC to determine the product, $^{64}$Cu-Sar-PSMA with >98% radiochemical purity.

Stability in Plasma

To 200 µL of fresh human plasma at 37° C. was added a solution of $^{64}$Cu-Sar-PSMA in saline (100 µL, ~8.8 MBq, <10% EtOH) and the mixture was incubated at 37° C. for 24 hours. After 24 hours, cold acetonitrile (600 µL) was added. The precipitated serum proteins were separated by centrifugation (13 000 rpm) and 300 µL of the supernatant was removed and concentrated by evaporation. The solution was diluted in water (100 µL) and the product analysed by RP-HPLC.

Tumour Imaging in LNCaP Tumor-Bearing Mice

The in vivo biodistribution of $^{64}$CuSarPSMA was investigated in LNCaP tumor-bearing NSG (NOD SCID Gamma) mice at 1 h, 6 h, and 22 h after injection. At 1 h, $^{64}$CuSarPSMA showed the highest uptake in the kidneys resulting in low tumor/kidney ratios (FIG. 5). However, the biodistribution data revealed rapid kidney clearance and moderate tumor retention at later timepoints. Despite the moderate retention of $^{64}$Cu-Sar-PSMA in the tumor, there was significant contrast due to rapid clearance from circulation and virtually no background accumulation after 6 h. Furthermore, low uptake in other PSMA-positive tissues (lung, spleen) allowed high tumor-to-background ratios for $^{64}$Cu-Sar-PSMA.

Example 2

Synthesis of CoSar(PSMA)$_2$

Synthesis of Activated Glu Intermediate

Reference: Duspara, P. A.; Islam, M. S.; Lough, A. J.; Batey, R. A., Synthesis and reactivity of N-alkyl carbamoylimidazoles: development of N-methyl carbamoylimidazole as a methyl isocyanate equivalent. *J Org Chem* 2012, 77 (22), 10362-8.

To a flask containing L-Bis(tbu)Glu HCl (3.56 g, 12.04 mmol, 1.0 eq) and carbonyl diimidazole (2.15 g, 13.24 mmol, 1.1 eq) was added a 1:5 mixture of DMF/MeCN (50 mL). The reaction was stirred overnight at $R_T$. After stirring, the solvent was removed in vacuo and the remaining crude mixture was dissolved and purified via flash chromatography (mobile phase: 7:3:1 petroleum spirits/chloroform/methanol, RF: ~0.24, 30:1 silica/crude mass ratio) to afford the product as a white semi-crystalline powder, (2.25 g, 52.9% yield).

Synthesis of Protected Urea

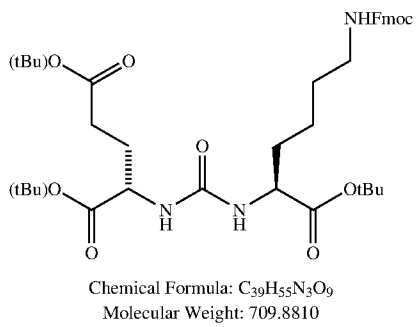

Chemical Formula: C$_{39}$H$_{55}$N$_3$O$_9$
Molecular Weight: 709.8810

To a flask containing H-Lys(Fmoc)-OtBu•HCl (4.84 g, 10.5 mmol, 1.0 eq) was added activated Glu intermediate (3.71 g, 10.5 mmol, 1.0 eq) and DIPEA (1.83 mL, 10.5 mmol, 1 eq) in DCM (30 mL) and stirred overnight at $R_T$. The reaction mixture was washed with water ×3, brine, and dried over MgSO$_4$ and loaded onto an 80 g Reveleris HP Silica cartridge and purified via Biotage Isolera automatic flash chromatography purification system (mobile phase: 70:30:2.5 petroleum spirits/chloroform/methanol). The fractions were analysed via TLC (mobile phase: 7:3:1 petroleum spirits/chloroform/methanol, RF: ~0.30), combined, and the solvent was removed in vacuo to afford the product as a yellow oil, 5.06 g, 68% yield. ESIMS+[M+H$^+$]m/z 710.386 (experimental), m/z 710.401 (calcd).

Fmoc Cleavage of Urea

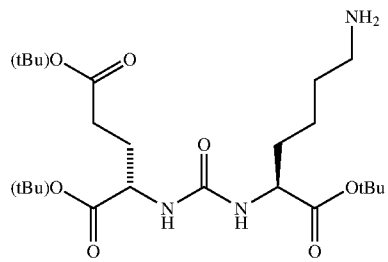

Chemical Formula: C$_{24}$H$_{46}$N$_3$O$_7$
Molecular Weight: 487.6380

To a flask containing the protected urea (5.06 g, 7.13 mmol, 1 eq) was added 20% diethylamine in MeCN (100 mL) and the reaction was stirred for 7 hours at RT. Aliquots were removed periodically to analyse via MS for completion of reaction. After 7 hours, the diethylamine and MeCN were reduced in vacuo to 5 mL, and an additional 50 mL of MeCN was added to azeotrope the diethylamine via rotary evaporator three times. The reaction mixture was reduced again to 5 mL, 200 mL of 50/50 water/MeCN was added and the reaction mixture was lyophilized. Due to impurities stemming from the incomplete scavenging of the dibenzofulvene moiety, the final product was used without further purification. (Estimated 70% purity) ESIMS+[M+H$^+$]m/z 488.329 (experimental), m/z 488.333 (calcd).

Synthesis of 8-Aoc-ff Linker on Resin

The 8-Aoc-ff linker was prepared using the following Fmoc protocol below.
General Fmoc Deprotection Protocol
The resin bound peptide was treated with a solution of 20% piperidine in DMF for 15 min×3. The resin was then washed consecutively with DMF×3 and DCM×3.
Protocol for Loading Fmoc-aminooctanoic Acid (Fmoc-8-Aoc-OH) to 2-CT Resin
Fmoc-8-Aoc-OH (5.00 g, 13.1 mmol, 1.75 eq) and DIPEA (2 eq relative to AA) in 80 mL DCM was added onto 2-CT resin (7.50 g, 1 mmol/g, 1 eq) and stirred. After 2 hr, 8 mL MeOH was added and the resin was stirred an additional 30 min. The resin was filtered and washed consecutively with DCM×3, DMF×3, DCM×3, MeOH×2, and Et$_2$O×2 and dried. Resin loading was calculated using the equation below, and was found to be 0.628 mmol/g (6.16 mmol in total)

$$\text{Resin Loading} = \frac{\text{final weight} - \text{initial weight}}{\text{MW of } Fmoc - 8 - Aoc - OH} \text{ mmol/g}$$

Protocol for Coupling Fmoc-D-Phe-OH to Resin
Fmoc-D-Phe-OH (2 eq) was activated using HATU (0.96 eq relative to AA) and DIPEA (2 eq. relative to AA) in NMP. After 5 min, the solution was added onto the resin and was stirred for a minimum of 12 hr. The resin was filtered and washed consecutively with DMF×1, DCM×3, and DMF×3. Then, the coupling was repeated as above for a minimum of 12 hr, before being filtered and washed consecutively with DMF×1, DCM×3, and DMF×3.
Resin Cleavage Protocol
The resin was washed several times with DCM and then transferred to two 50 mL falcon tubes. 5% TFA in DCM (75 mL) was added and the resin was agitated at $R_T$ for 2 h. The resin was filtered and washed twice with 15 mL 5% TFA in DCM. The filtrate was collected and the solvent was reduced under a stream of N$_2$. The crude peptide was redissolved in 50/50 water/MeCN and lyophilized to afford the crude peptide. The crude peptide was used without further purification.
Trifluoroacetamide Protection

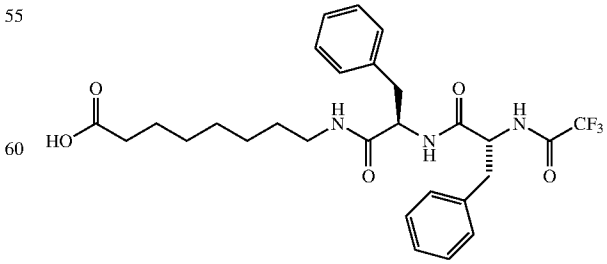

Chemical Formula: C$_{28}$H$_{34}$F$_3$N$_3$O$_5$
Molecular Weight: 549.5912

To a flask containing the crude peptide linker (1.35 g, 2.98 mmol if pure, 1 eq) was added ethyl trifluoroacetate (0.532 mL, 4.47 mmol, 1.5 eq) and DIPEA (1.04 mL, 5.96 mmol, 2 eq) in MeOH (10 mL). The reaction was stirred overnight at $R_T$ and monitored via MS and analytical HPLC for complete conversion of starting material. The MeOH was reduced in vacuo and EtOAc/0.01 M HCl was added to the reaction. The organic layer was separated and washed with 0.01 M HCl×3 and brine, dried over $MgSO_4$ and the solvent was removed in vacuo and dried to afford the crude product (0.985 g) that was used without further purification. Orbitrap-MS$^+$[M+H$^+$]m/z 550.253 (experimental), m/z 550.252 (calcd), [2M+H$^+$]m/z 1099.498 (experimental), m/z 1099.497 (calcd).

Urea-Linker Coupling

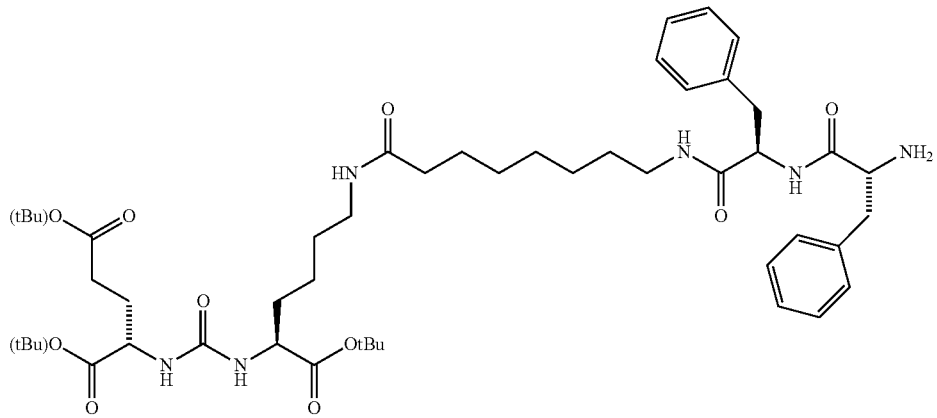

Chemical Formula: $C_{50}H_{78}N_6O_{10}$
Molecular Weight: 923.2060

To a flask containing the crude TFA-protected linker (0.985 g, 1.79 mmol if pure, 1 eq) was added HATU (0.608 g, 1.6 mmol, 0.89 eq) and DIPEA (0.56 mL, 3.2 mmol, 1.79 eq) in DMF (5 mL) and stirred at RT. After 5 minutes, the deprotected urea (approx. 1.5 mmol) was added and the reaction was monitored via MS and analytical HPLC overnight. After 24 hr, $K_2CO_3$ in water was added and the reaction was heated to 60° C. overnight and monitored for removal of the trifluoroacetamide protecting group. The reaction was diluted with water (150 mL) and extracted with $Et_2O$×3. The ether fractions were combined and washed with water, 0.01 M HCl×3, and brine, and dried over $MgSO_4$. The aqueous layer was acidified with 0.1 M HCl and extracted with $Et_2O$, washed with water, 0.01 M HCl, and brine, and dried over $MgSO_4$. The ether layers were combined, the solvent was removed in vacuo, and the crude product was dissolved in 80% MeCN in water and purified via RP-HPLC (60-77% over 35 min) on a Phenomenex Luna 5 μ 100 Å C18 21.2×250 mm semi-preparative column at 8 mL/min. The fractions containing the product were collected and lyophilized to afford the product as a fluffy white powder (49.6 mg, 98%+ purity). Orbitrap-MS+[M+H$^+$]m/z 923.586 (experimental), m/z 923.585 (calcd), [M+2H$^+$]m/z 462.297 (experimental), m/z 462.296 (calcd).

Synthesis of (tBoc)$_4$-sCoSar-Plus (tBoc)$_{4-5}$CoSar-Plus can be prepared according to procedures in Ma, M. T.; Cooper, M. S.; Paul, R. L.; Shaw, K. P.; Karas, J. A.; Scanlon, D.; White, J. M.; Blower, P. J.; Donnelly, P. S. *Inorg Chem* 2011, 50, 6701.

Synthesis of CoSar-(PSMA)$_2$

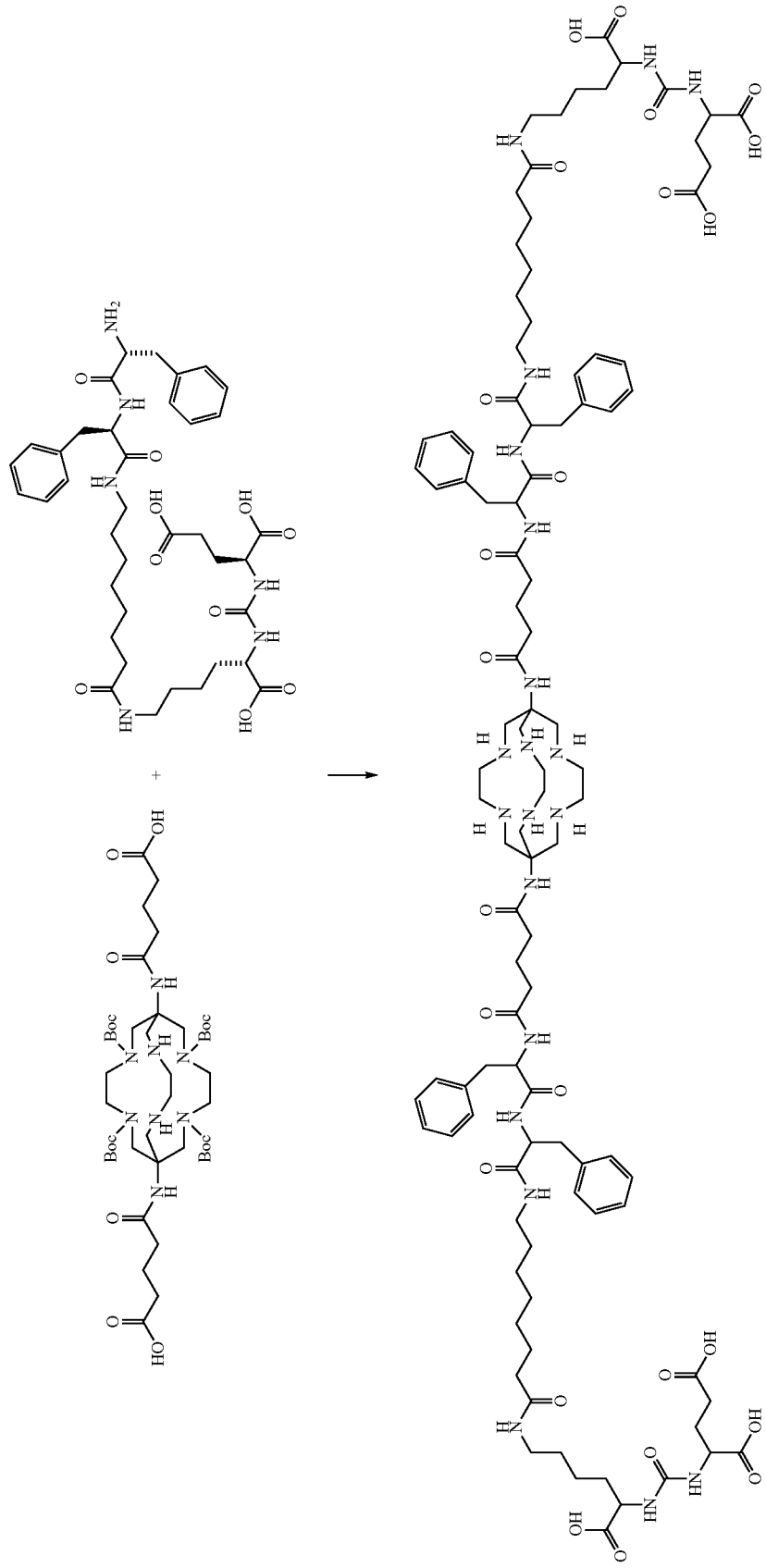

To an Eppendorf tube was added (tBoc)$_{4-5}$COSar-Plus (25.3 mg, 0.027 mmol, 1 eq), HATU (20.4 mg, 0.054 mmol, 2 eq), and DIPEA (18.7 µL, 0.107 mmol, 4 eq.) in NMP (500 µL). The mixture was shaken for 10 minutes to allow for activation and then added to a 2 mL microwave vial containing the pure PSMA Linker-Urea (49.6 mg, 0.054 mmol, 2 eq) in NMP (400 µL). The reaction was stirred in the microwave reactor at 60° C. for 10 minutes, cooled, and analysed via MS and analytical HPLC to show complete consumption of starting material. To the reaction material was added 1.8 mL 72% MeCN in water and purified via RP-HPLC (60-90% over 60 min) on a Phenomenex Luna 5 µ 100 Å C18 21.2×250 mm semi-preparative column at 8 mL/min. The fractions containing the product were collected and lyophilized to afford the protected product as a fluffy white powder (14.0 mg, 5.08 µmol, 18.9% yield). The protected product was dissolved in 95% TFA in water overnight, diluted with 50/50 MeCN/water, and lyophilized to afford the product as a white powder as the tris-trifluoroacetate monohydrate salt (12.1 mg, 5.08 µmol) (rt: 10.3 min, 96.4% purity). Orbitrap-MS+[M+2H$^+$]m/z 1009.065 (experimental), m/z 1009.066 (calcd), [M+3H$^+$]m/z 673.046 (experimental), m/z 673.046 (calcd).

Radiolabeling

An aliquot of $^{64}$Cu$^{II}$ (100-400 MBq, 0.01 M HC) was added to a solution containing 0.1 M NH$_4$OAc, pH 5.5 (500 µL), ethanol (100 µL), MilliQ water (300 µL), and gentisic acid (1.2 mg, 10 mg/mL in MilliQ water) and the pH was measured (pH: 5). To this solution was added CoSar-(PSMA)$_2$ (20 µg, 8.4×10$^3$ µmol, 1 mg/mL in MilliQ) and the reaction was incubated for 30 min at room temperature. After 30 minutes, an aliquot was analysed by RP-HPLC to determine the product, $^{64}$Cu-CoSar(PSMA)$_2$ with >97% radiochemical purity (rt: 13.9 min).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A method for the treatment of a cancer, the method comprising administering to a subject in need thereof a compound of Formula (I), or a salt, complex, or solvate thereof:

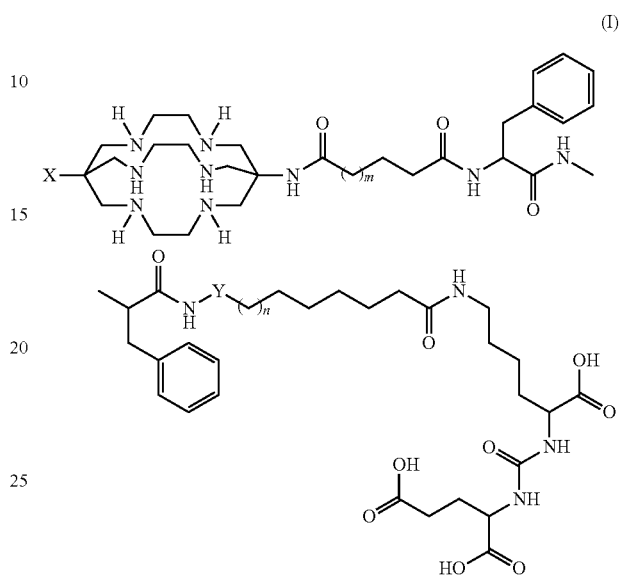

wherein:
X is a group selected from H, OH, halogen, cyano, NO$_2$, NH$_2$, optionally substituted C$_1$-C$_{12}$ alkyl, optionally substituted amino, optionally substituted amide and optionally substituted aryl;
Y is an optionally substituted C$_1$-C$_{12}$ alkylene group, wherein one or more of the methylene groups in the alkylene group may be further optionally substituted for a group selected from amide, carbonyl, urea and thiourea;
m is 0, 1, or 2; and
n is 0, 1, or 2;
wherein the compound of Formula (I) is complexed with a radionuclide of a metal selected from the group consisting of Cu, Tc, Ga, Co, In, Fe and Ti.

2. A method according to claim 1, wherein the radionuclide is a Cu ion.

3. A method according to claim 1, wherein the radionuclide is selected from the group consisting of $^{60}$Cu, $^{61}$Cu, $^{62}$Cu, $^{64}$Cu and $^{67}$Cu.

4. A method according to claim 1, wherein the radionuclide is $^{67}$Cu.

5. A method according to claim 1, wherein the compound of Formula (I) has the following structure:

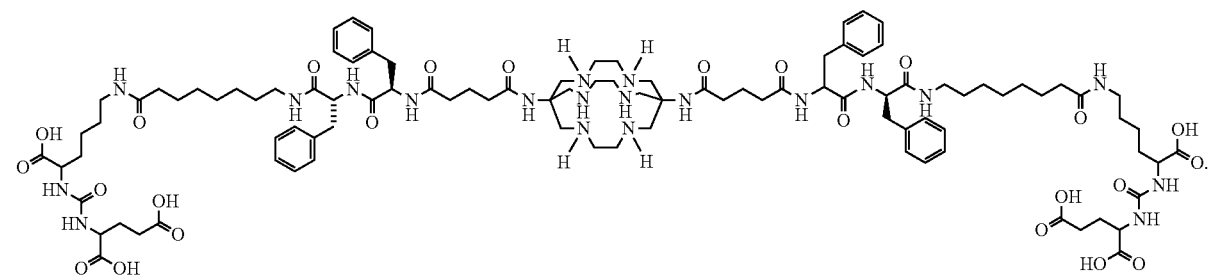 [SMILES: O=C(O)CCC(NC(=O)NC(CCCCNC(=O)CCCCCCCNC(=O)[C@@H](Cc1ccccc1)NC(=O)C(Cc1ccccc1)NC(=O)CCCC(=O)NC12CNCCNCC(NC(=O)CCCC(=O)N[C@H](Cc3ccccc3)C(=O)N[C@H](Cc3ccccc3)C(=O)NCCCCCCCC(=O)NCCCCC(NC(=O)NC(CCC(=O)O)C(=O)O)C(=O)O)(CNCCNC1)CNCCNC2)C(=O)O)C(=O)O]

6. A method according to claim 1, wherein the cancer is a prostate cancer.

7. A method for the treatment of a metastatic cancer, the method comprising administering to a subject in need thereof a compound of Formula (I), or a salt, complex, or solvate thereof:

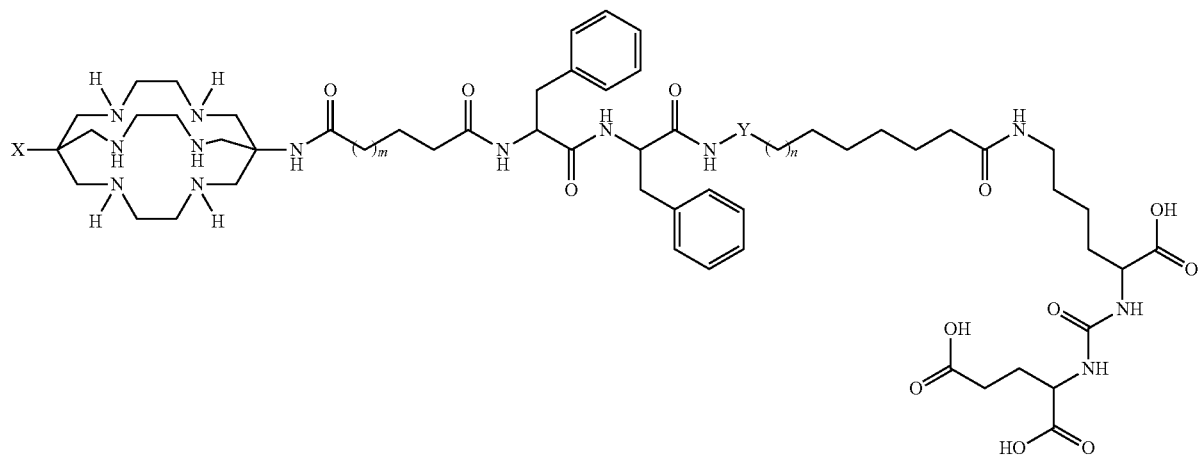

(I)

wherein:

X is a group selected from H, OH, halogen, cyano, $NO_2$, $NH_2$, optionally substituted $C_1$-$C_{12}$ alkyl, optionally substituted amino, optionally substituted amide and optionally substituted aryl;

Y is an optionally substituted $C_1$-$C_{12}$ alkylene group, wherein one or more of the methylene groups in the alkylene group may be further optionally substituted for a group selected from amide, carbonyl, urea and thiourea;

m is 0, 1, or 2; and n is 0, 1, or 2;

wherein the compound of Formula (I) is complexed with a radionuclide of a metal selected from the group consisting of Cu, Tc, Ga, Co, In, Fe and Ti; and wherein the metastatic cancer is associated with expression of PSMA.

8. A method according to claim 7, wherein the radionuclide is a Cu ion.

9. A method according to claim 7, wherein the radionuclide is selected from the group consisting of $^{60}$Cu, $^{61}$Cu, $^{62}$Cu, $^{64}$Cu and $^{67}$Cu.

10. A method according to claim 7, wherein the radionuclide is $^{67}$Cu.

11. A method according to claim 7, wherein the compound of Formula (I) has the following structure:

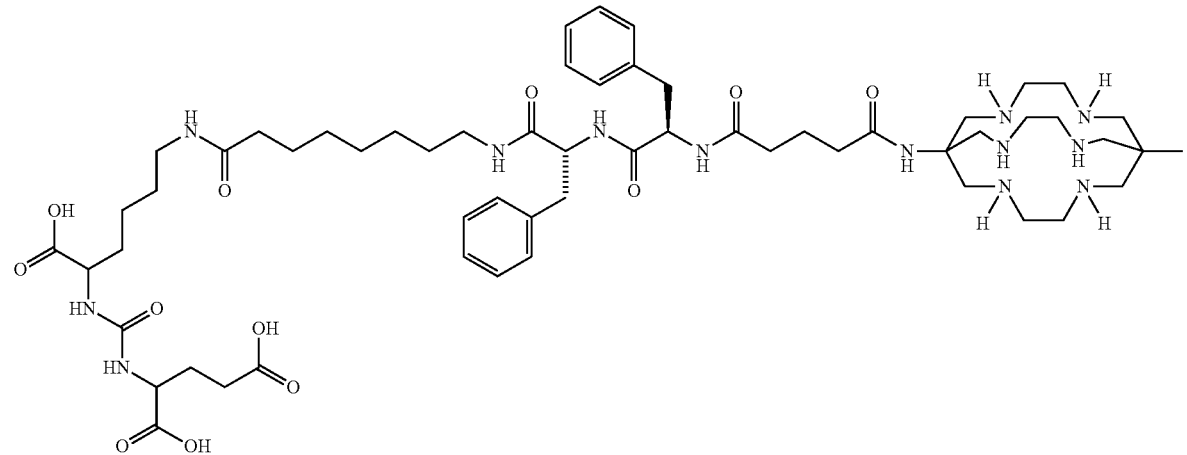

-continued

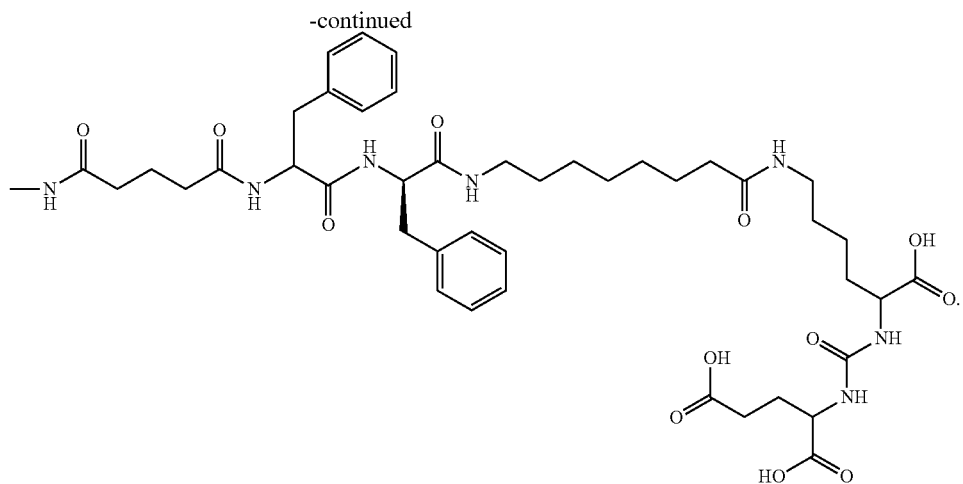

12. A method according to claim 7, wherein the metastatic cancer is a metastatic prostate cancer.

13. A method for the radioimaging of a cancer, the method comprising administering to a subject in need thereof a compound of Formula (I), or a salt, complex, or solvate thereof:

(I)

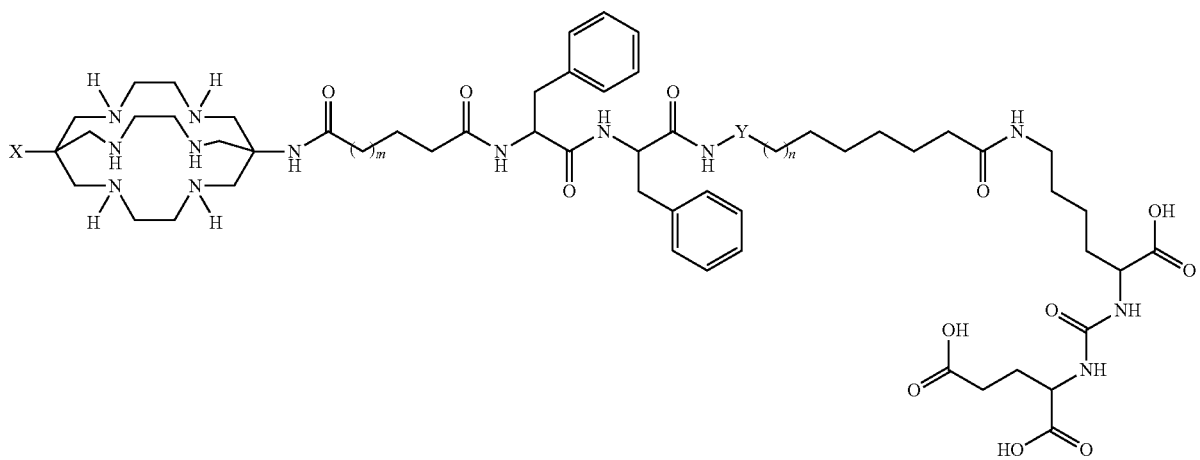

wherein:
X is a group selected from H, OH, halogen, cyano, $NO_2$, $NH_2$, optionally substituted $C_1$-$C_{12}$ alkyl, optionally substituted amino, optionally substituted amide and optionally substituted aryl;
Y is an optionally substituted $C_1$-$C_{12}$ alkylene group, wherein one or more of the methylene groups in the alkylene group may be further optionally substituted for a group selected from amide, carbonyl, urea and thiourea;
m is 0, 1, or 2; and
n is 0, 1, or 2;
wherein the compound of Formula (I) is complexed with a radionuclide of a metal selected from the group consisting of Cu, Tc, Ga, Co, In, Fe and Ti;

wherein the method further comprises obtaining one or images from the subject by positron emission tomography (PET) or single-photon emission computed tomography (SPECT).

14. A method according to claim 13, wherein the radionuclide is a Cu ion.

15. A method according to claim 13, wherein the radionuclide is selected from the group consisting of $^{60}$Cu, $^{61}$Cu, $^{62}$Cu, $^{64}$Cu and $^{67}$Cu.

16. A method according to claim 13, wherein the radionuclide is $^{64}$Cu.

17. A method according to claim 13, wherein the cancer is associated with expression of PSMA.

18. A method according to claim 13, wherein the cancer is a prostate cancer.

19. A method according to claim 13, wherein the cancer is a metastatic prostate cancer.

20. A method according to claim 13, wherein the compound of Formula (I) has the following structure:

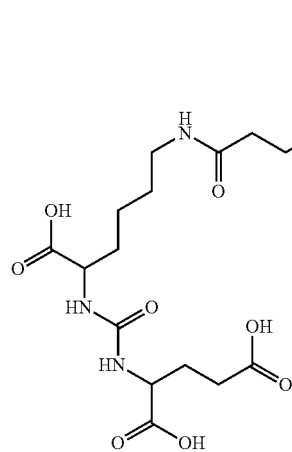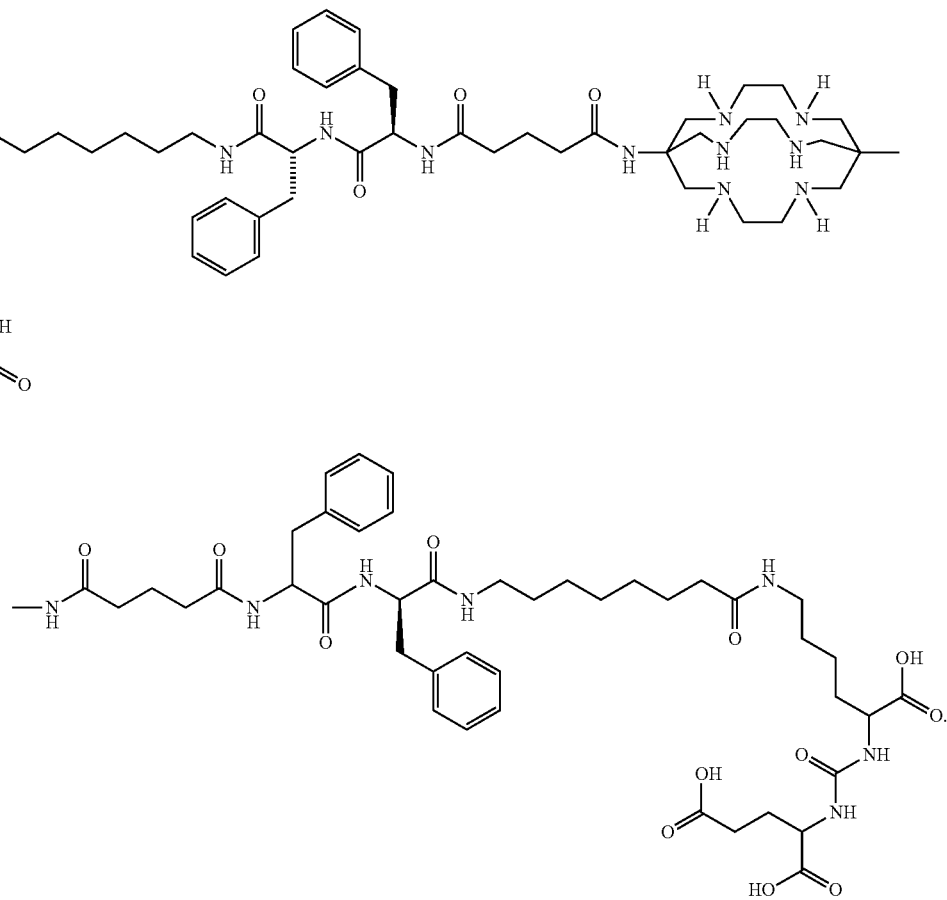
* * * * *